(12) United States Patent
Shluzas

(10) Patent No.: US 7,618,444 B2
(45) Date of Patent: Nov. 17, 2009

(54) SURGICAL INSTRUMENT FOR MOVING A VERTEBRA

(75) Inventor: Alan E. Shluzas, Millis, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 180 days.

(21) Appl. No.: 10/939,935

(22) Filed: Sep. 13, 2004

(65) Prior Publication Data

US 2005/0033299 A1 Feb. 10, 2005

Related U.S. Application Data

(63) Continuation of application No. PCT/US03/27879, filed on Sep. 5, 2003, which is a continuation-in-part of application No. 10/236,713, filed on Sep. 6, 2002, now Pat. No. 6,648,888.

(51) Int. Cl.
*A61B 17/88* (2006.01)
(52) U.S. Cl. .................. 606/279; 606/264; 606/86 A
(58) Field of Classification Search .......... 606/61, 606/72, 73, 90, 99, 60, 246–279, 300–301, 606/309, 104, 86 A, 914, 916, 198, 108; 623/17.11–17.16; 604/104, 106; 600/219, 220, 222
See application file for complete search history.

(56) References Cited

U.S. PATENT DOCUMENTS

| 3,044,461 A | 7/1962 | Murdock |
|---|---|---|
| 3,789,852 A | 2/1974 | Kim et al. |
| 3,960,147 A | 6/1976 | Murray |
| 4,545,374 A | 10/1985 | Jacobson |
| 4,601,713 A | 7/1986 | Fuqua |
| 4,611,581 A | 9/1986 | Steffee |

(Continued)

FOREIGN PATENT DOCUMENTS

EP 0528562 A2 2/1993

(Continued)

OTHER PUBLICATIONS

Medtronic Sofamor Danek presentation materials entitled *CD Horizon® Spinal System Surgical Technique*, dated 2001 (pp. 7, 16-22). This is of record in U.S. Appl. No. 10/236,713, now U.S. Patent No. 6,648,888.

(Continued)

*Primary Examiner*—Thomas C Barrett
*Assistant Examiner*—James L Swiger
(74) *Attorney, Agent, or Firm*—Crompton, Seager & Tufte, LLC

(57) ABSTRACT

A surgical instrument includes a first device adapted to be connected to a fastener fixed to a first bone portion. A second device includes a first portion associated with the first device and a second portion for supporting a member which engages the fastener fixed to the first bone portion and secures a rod connected to the second bone portion to the fastener. The second portion is adapted for pressing the member against the rod. The first device has a part that prevents the second device from moving toward the fastener that is connected to the first device so that the member is rotated relative to the fastener but is not moved axially relative to the fastener in response to rotation of the second device.

21 Claims, 28 Drawing Sheets

U.S. PATENT DOCUMENTS

| | | | |
|---|---|---|---|
| 4,716,901 A | 1/1988 | Jackson et al. | |
| 4,819,620 A | 4/1989 | Okutsu | |
| 4,921,478 A | 5/1990 | Solano et al. | |
| 4,984,564 A | 1/1991 | Yuen | |
| 5,020,519 A | 6/1991 | Hayes et al. | |
| 5,025,778 A | 6/1991 | Silverstein et al. | |
| 5,131,382 A | 7/1992 | Meyer | |
| 5,139,499 A | 8/1992 | Small et al. | |
| 5,163,949 A | 11/1992 | Bonutti | |
| 5,171,279 A | 12/1992 | Mathews | |
| 5,190,561 A | 3/1993 | Graber | |
| 5,195,541 A | 3/1993 | Obenchain | |
| 5,197,971 A | 3/1993 | Bonutti | |
| 5,224,680 A | 7/1993 | Greenstein et al. | |
| 5,287,845 A | 2/1994 | Faul et al. | |
| 5,295,994 A | 3/1994 | Bonutti | |
| 5,312,417 A | 5/1994 | Wilk | |
| 5,354,302 A | 10/1994 | Ko | |
| 5,370,647 A | 12/1994 | Graber et al. | |
| 5,375,956 A | 12/1994 | Pennig | |
| 5,395,317 A | 3/1995 | Kambin | |
| 5,439,464 A | 8/1995 | Shapiro | |
| 5,454,365 A | 10/1995 | Bonutti | |
| 5,472,426 A | 12/1995 | Bonati et al. | |
| 5,484,437 A | 1/1996 | Michelson | |
| 5,484,440 A * | 1/1996 | Allard | 606/73 |
| 5,489,307 A | 2/1996 | Kuslich et al. | |
| 5,520,607 A | 5/1996 | Frassica et al. | |
| 5,571,072 A | 11/1996 | Kronner | |
| 5,575,754 A | 11/1996 | Konomura | |
| 5,601,556 A * | 2/1997 | Pisharodi | 606/61 |
| 5,601,590 A | 2/1997 | Bonutti et al. | |
| 5,667,520 A | 9/1997 | Bonutti | |
| 5,707,359 A | 1/1998 | Bufalini | |
| 5,720,751 A * | 2/1998 | Jackson | 606/86 |
| 5,782,831 A | 7/1998 | Sherman et al. | |
| 5,792,044 A | 8/1998 | Foley et al. | |
| 5,795,289 A | 8/1998 | Wyttenbach | |
| 5,827,319 A | 10/1998 | Carlson et al. | |
| 5,899,901 A | 5/1999 | Middleton | |
| 5,902,231 A | 5/1999 | Foley et al. | |
| 5,910,141 A | 6/1999 | Morrison et al. | |
| 5,954,635 A | 9/1999 | Foley et al. | |
| 5,961,499 A | 10/1999 | Bonutti et al. | |
| 5,997,508 A | 12/1999 | Lunn et al. | |
| 6,120,437 A | 9/2000 | Yoon et al. | |
| 6,123,707 A | 9/2000 | Wagner | |
| 6,162,236 A | 12/2000 | Osada | |
| 6,171,299 B1 | 1/2001 | Bonutti | |
| 6,187,000 B1 * | 2/2001 | Davison et al. | 606/1 |
| 6,251,111 B1 | 6/2001 | Barker et al. | |
| 6,261,296 B1 | 7/2001 | Aebi et al. | |
| 6,287,307 B1 | 9/2001 | Abboudi | |
| 6,306,170 B2 | 10/2001 | Ray | |
| 6,312,443 B1 | 11/2001 | Stone | |
| 6,338,730 B1 | 1/2002 | Bonutti et al. | |
| 6,358,266 B1 | 3/2002 | Ryan | |
| 6,361,488 B1 | 3/2002 | Davison et al. | |
| 6,371,968 B1 | 4/2002 | Kogasaka et al. | |
| 6,379,356 B1 | 4/2002 | Jackson | |
| 6,383,195 B1 | 5/2002 | Richard | |
| 6,440,133 B1 | 8/2002 | Beale et al. | |
| 6,491,695 B1 * | 12/2002 | Roggenbuck | 606/61 |
| 6,494,893 B2 | 12/2002 | Dubrul et al. | |
| 6,497,654 B1 | 12/2002 | Leonard et al. | |
| 6,524,320 B2 | 2/2003 | DiPoto | |
| 6,530,880 B2 | 3/2003 | Pagliuca | |
| 6,564,078 B1 | 5/2003 | Marino et al. | |
| 6,648,888 B1 | 11/2003 | Shluzas | |
| 6,652,553 B2 | 11/2003 | Davison et al. | |
| 6,660,006 B2 * | 12/2003 | Markworth et al. | 606/61 |
| 6,743,231 B1 * | 6/2004 | Gray et al. | 606/61 |
| 6,746,454 B2 | 6/2004 | Winterbottom et al. | |
| 6,755,841 B2 | 6/2004 | Fraser et al. | |
| 6,830,573 B2 * | 12/2004 | Strong et al. | 606/73 |
| 7,223,278 B2 * | 5/2007 | Davison et al. | 606/198 |
| 2001/0011170 A1 | 8/2001 | Davison et al. | |
| 2001/0021853 A1 * | 9/2001 | Heckele et al. | 606/99 |
| 2002/0002360 A1 | 1/2002 | Orth et al. | |
| 2002/0095153 A1 * | 7/2002 | Jones et al. | 606/61 |
| 2003/0009130 A1 | 1/2003 | Stecker et al. | |
| 2003/0014068 A1 | 1/2003 | Bonutti et al. | |
| 2003/0023243 A1 | 1/2003 | Biedermann et al. | |
| 2003/0040656 A1 | 2/2003 | Pagliuca et al. | |
| 2003/0073998 A1 | 4/2003 | Pagliuca et al. | |
| 2003/0125750 A1 * | 7/2003 | Zwirnmann et al. | 606/104 |
| 2003/0139648 A1 | 7/2003 | Foley et al. | |
| 2003/0153927 A1 | 8/2003 | DiPoto et al. | |
| 2003/0191371 A1 * | 10/2003 | Smith et al. | 600/210 |
| 2003/0195405 A1 | 10/2003 | Marino et al. | |
| 2003/0195493 A1 | 10/2003 | Davison et al. | |
| 2003/0195549 A1 | 10/2003 | Davison et al. | |
| 2003/0195550 A1 | 10/2003 | Davison et al. | |
| 2003/0195551 A1 | 10/2003 | Davison et al. | |
| 2003/0199871 A1 | 10/2003 | Foley et al. | |
| 2003/0199885 A1 | 10/2003 | Davison et al. | |
| 2003/0225408 A1 * | 12/2003 | Nichols et al. | 606/61 |
| 2003/0236529 A1 | 12/2003 | Shluzas et al. | |
| 2004/0024411 A1 | 2/2004 | Newton et al. | |
| 2004/0059339 A1 | 3/2004 | Roehm, III et al. | |
| 2004/0249378 A1 * | 12/2004 | Saint Martin et al. | 606/61 |

FOREIGN PATENT DOCUMENTS

| | | |
|---|---|---|
| EP | 0807415 A2 | 11/1997 |
| EP | 0807415 A3 | 8/1998 |
| EP | 0 980 677 | 2/2000 |
| EP | 1251767 A2 | 10/2002 |
| EP | 1305077 A1 | 5/2003 |
| FR | 2701379 | 8/1994 |
| JP | 2000083960 A2 | 3/2000 |
| JP | 2001149376 A2 | 6/2001 |
| WO | WO 92/21292 A2 | 10/1992 |
| WO | WO 93/14801 | 8/1993 |
| WO | WO 94/03114 | 2/1994 |
| WO | WO 95/10218 A1 | 4/1995 |
| WO | WO 95/32663 | 12/1995 |
| WO | WO 01/54560 A3 | 8/2001 |
| WO | WO 02/09801 A1 | 2/2002 |
| WO | WO 02/078767 A2 | 10/2002 |
| WO | WO 03/007783 A2 | 1/2003 |
| WO | WO 04/000145 A1 | 12/2003 |
| WO | WO 2004/022108 A3 | 3/2004 |

OTHER PUBLICATIONS

Synthesis® Spine presentation materials entitled *Click X™ Spondylolisthesis System 2001*, dated 2001. This is of record in U.S. Appl. No. 10/236,713, now U.S. Patent No. 6,648,888.

* cited by examiner

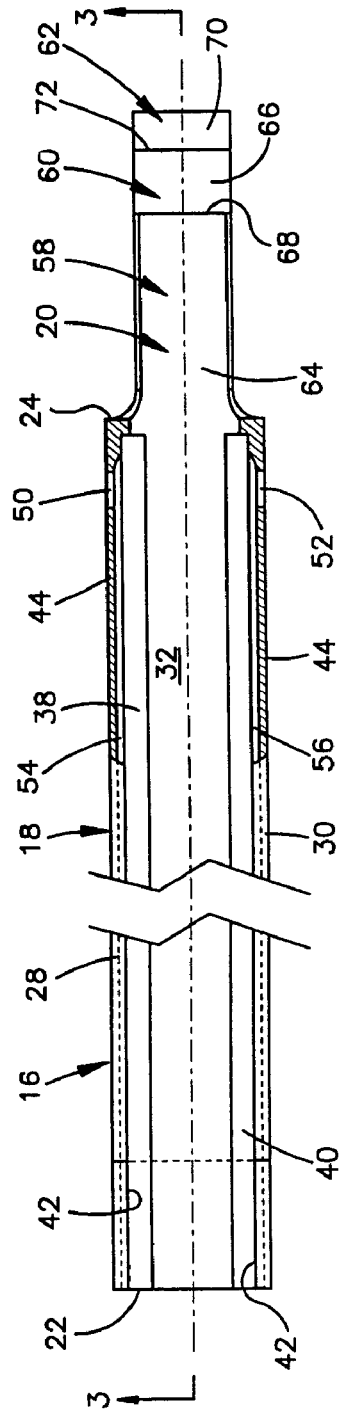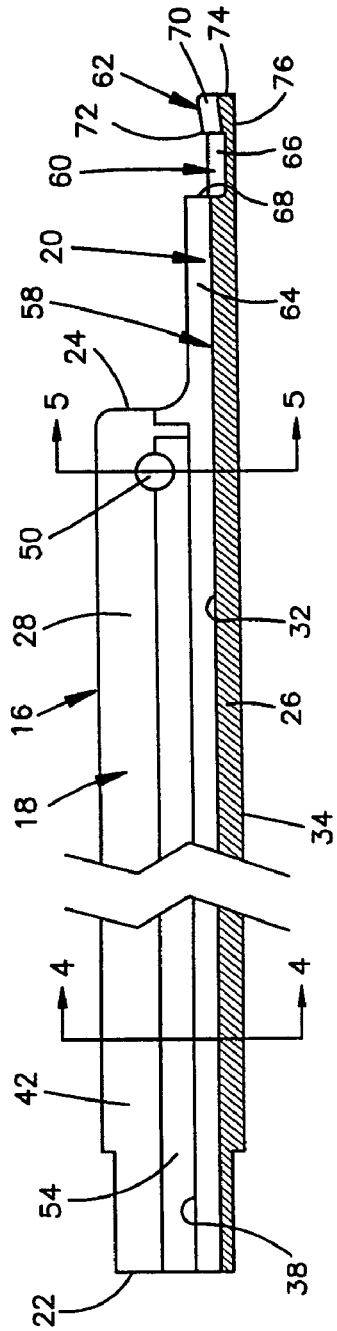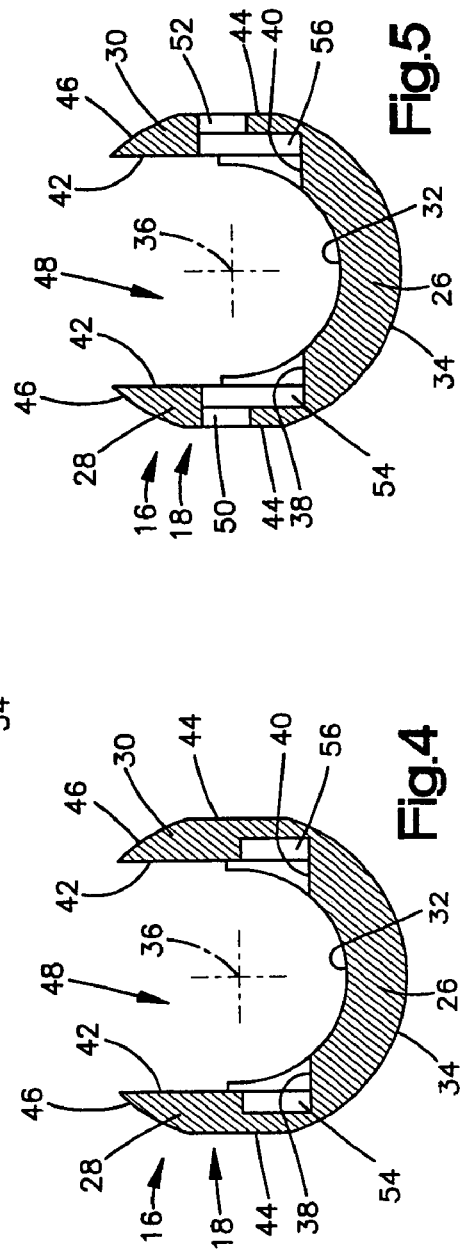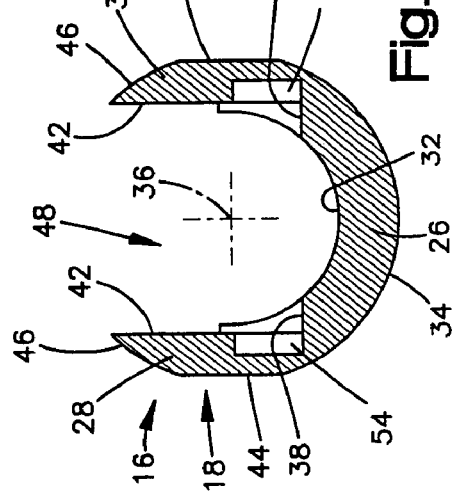

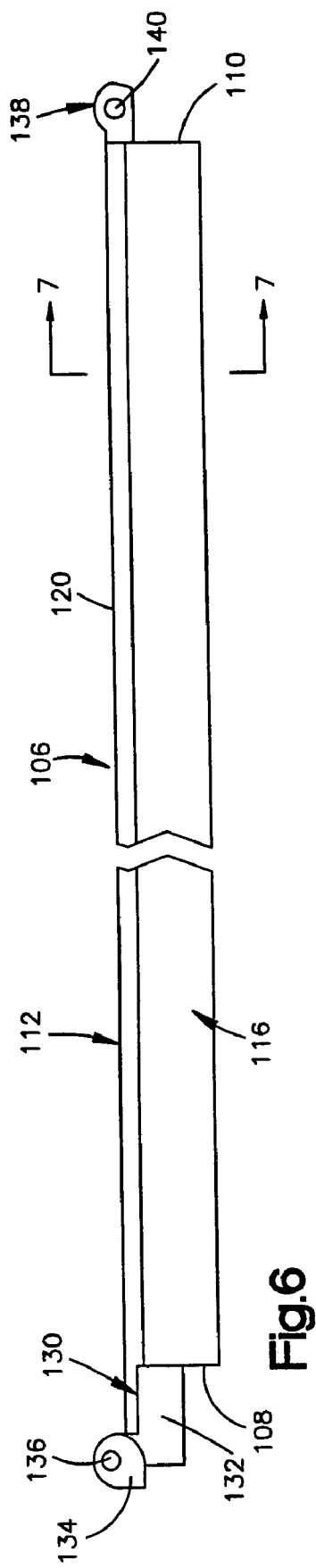
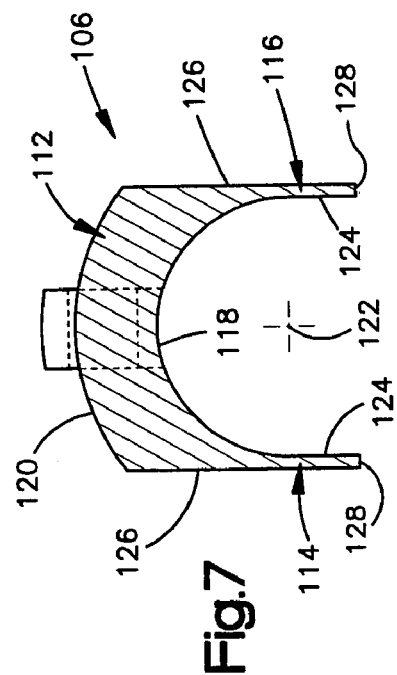

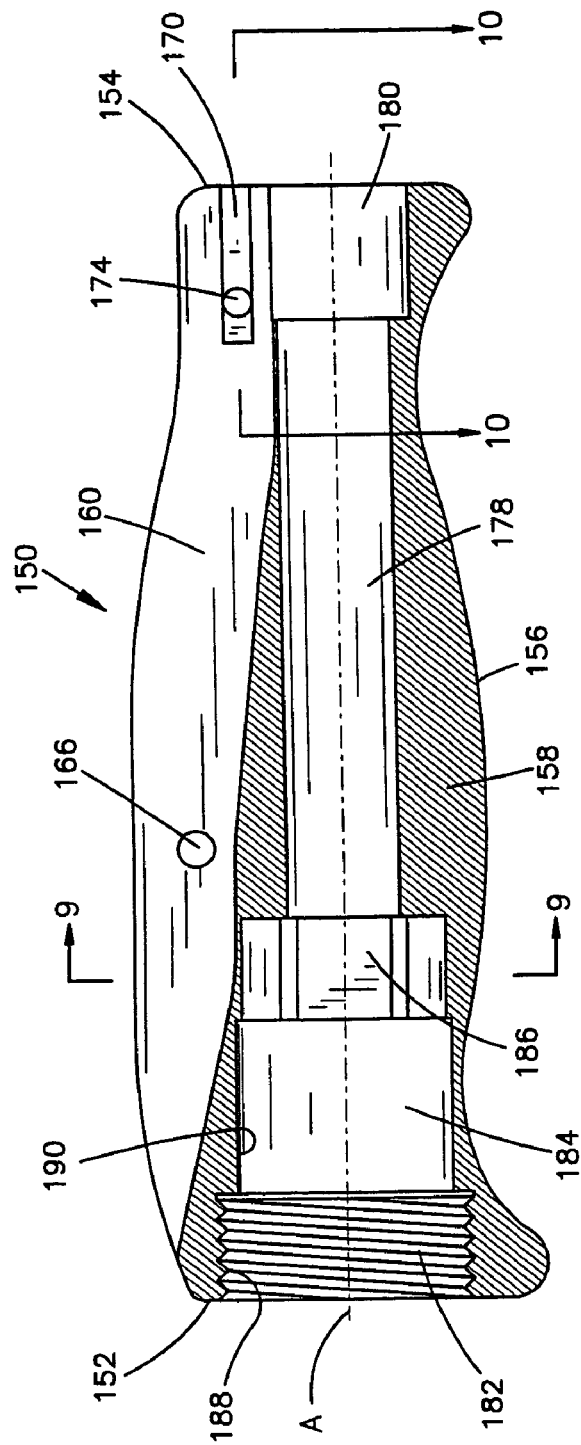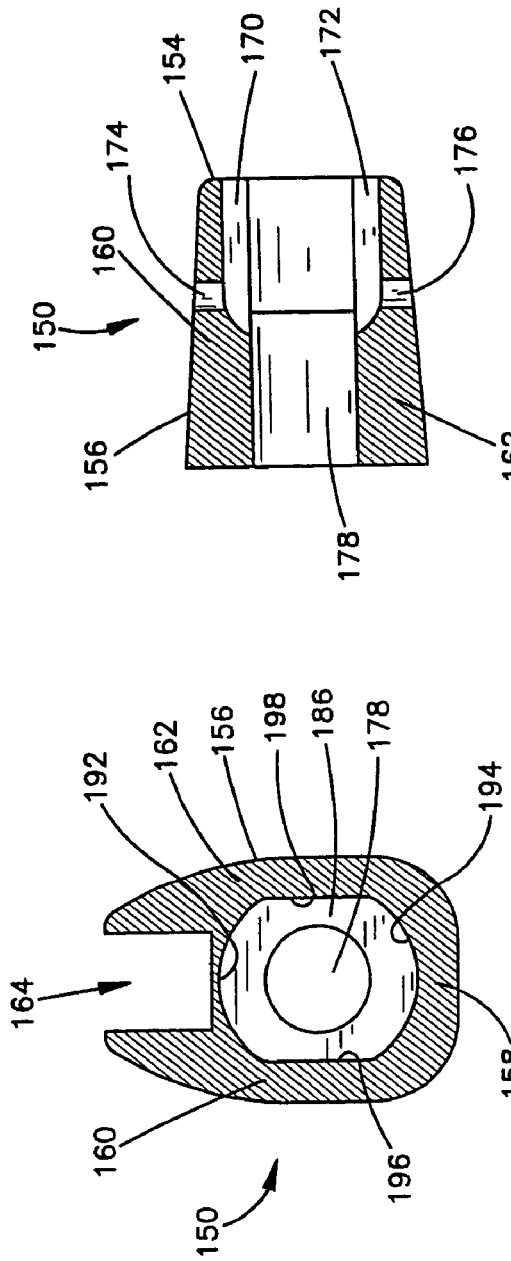

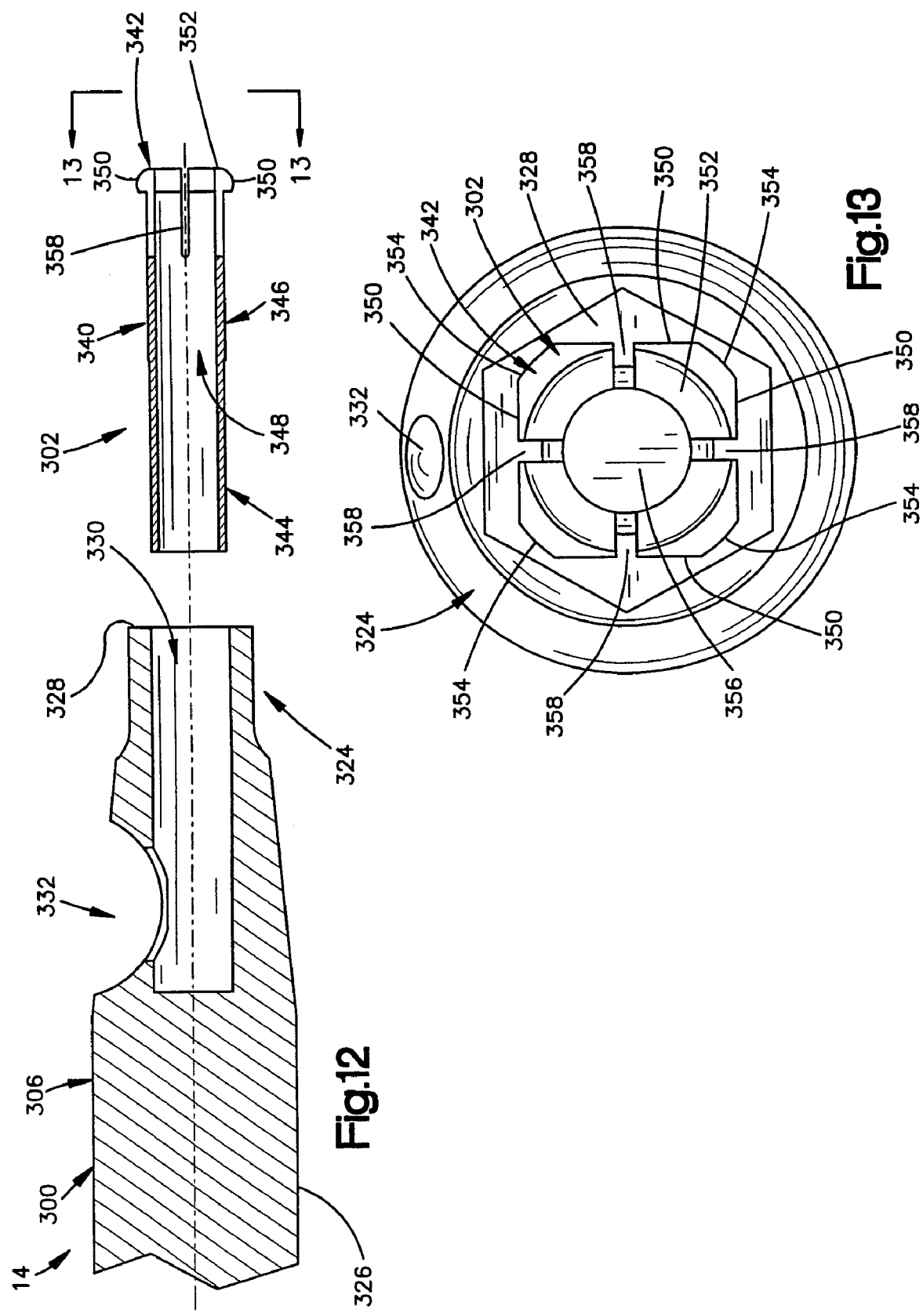

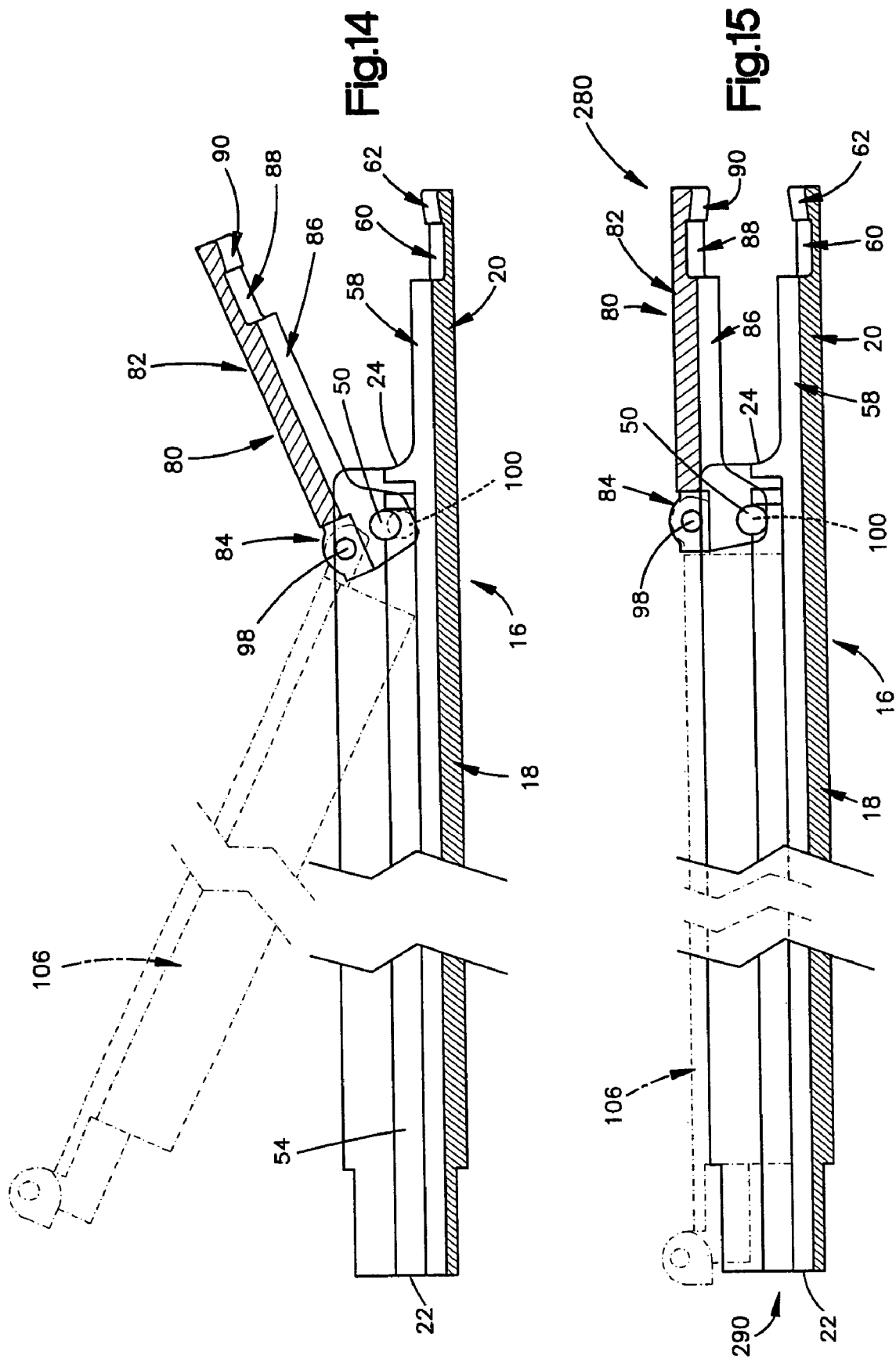

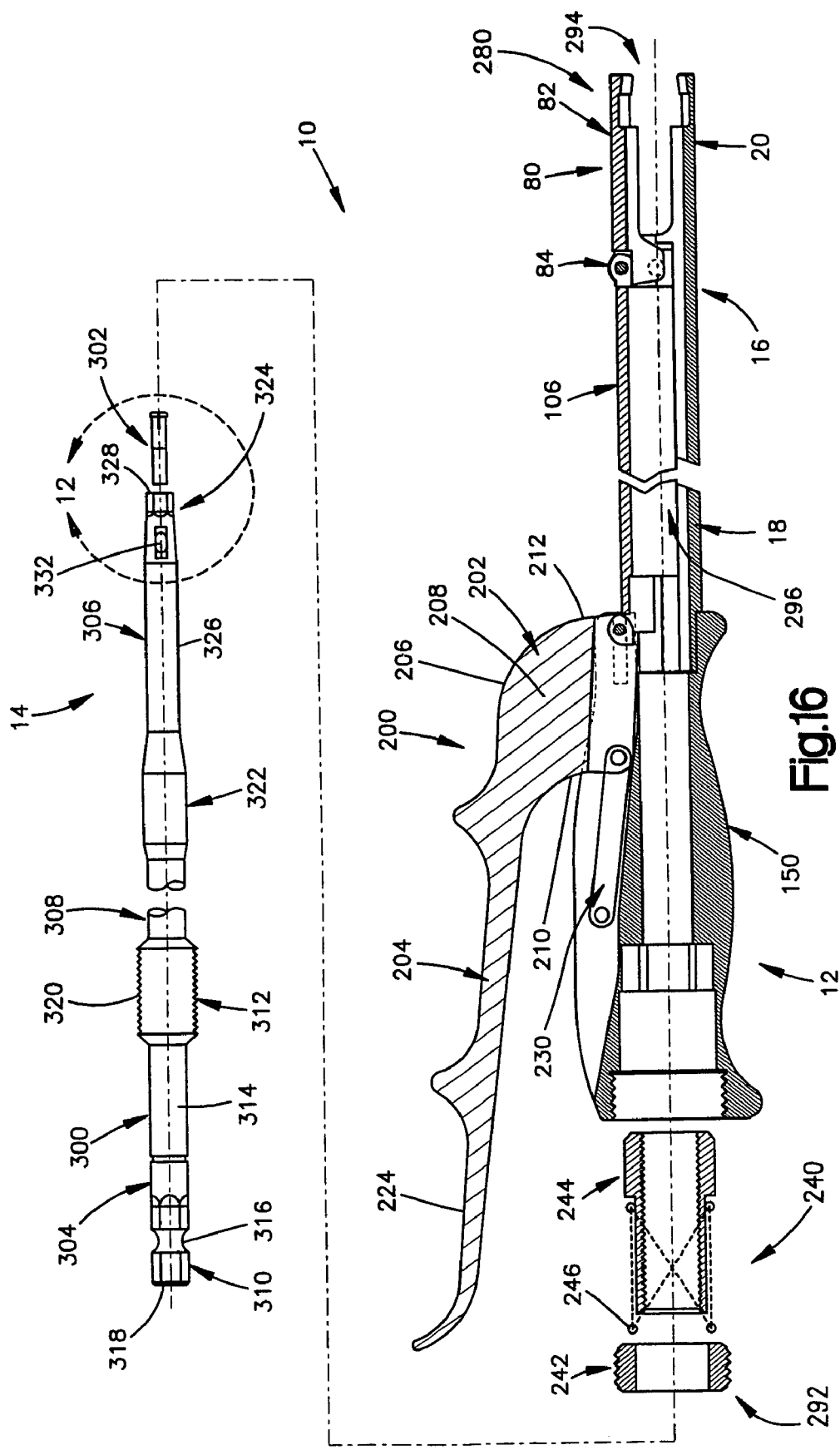

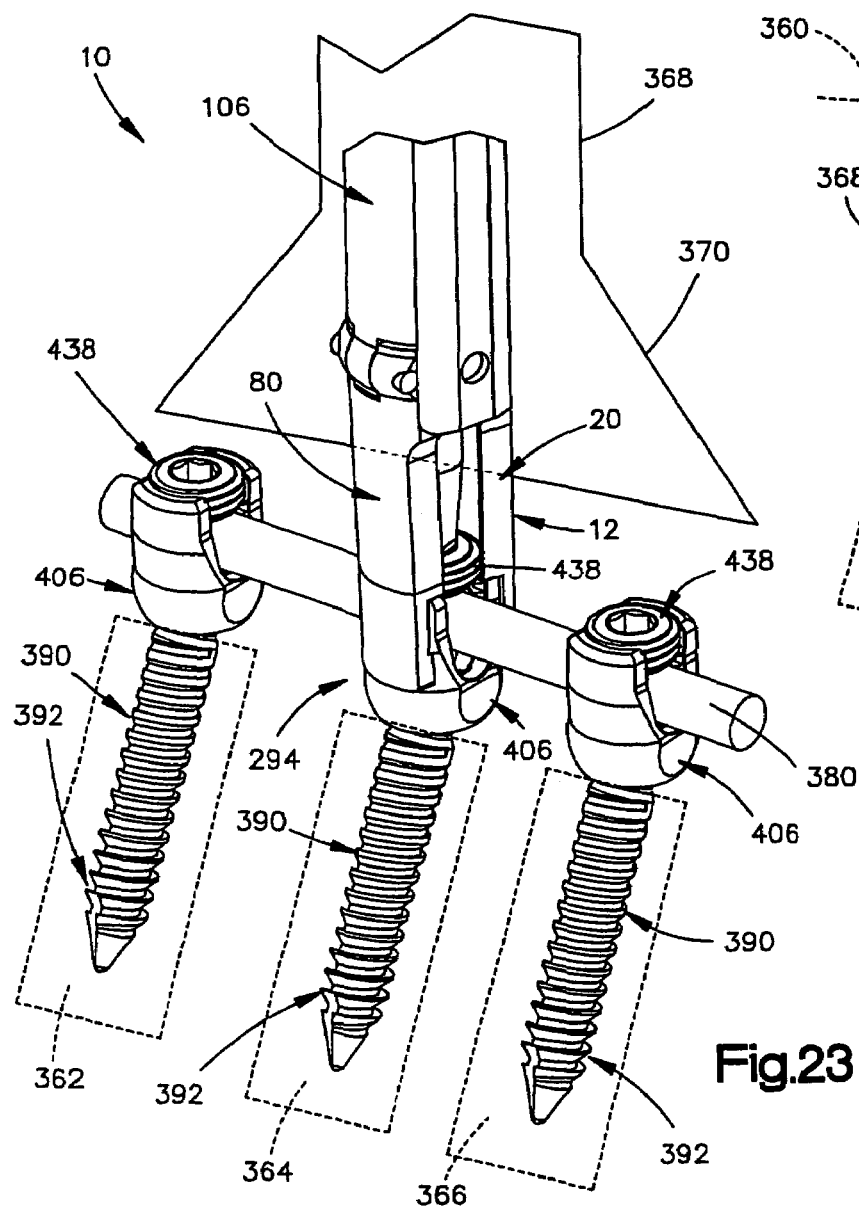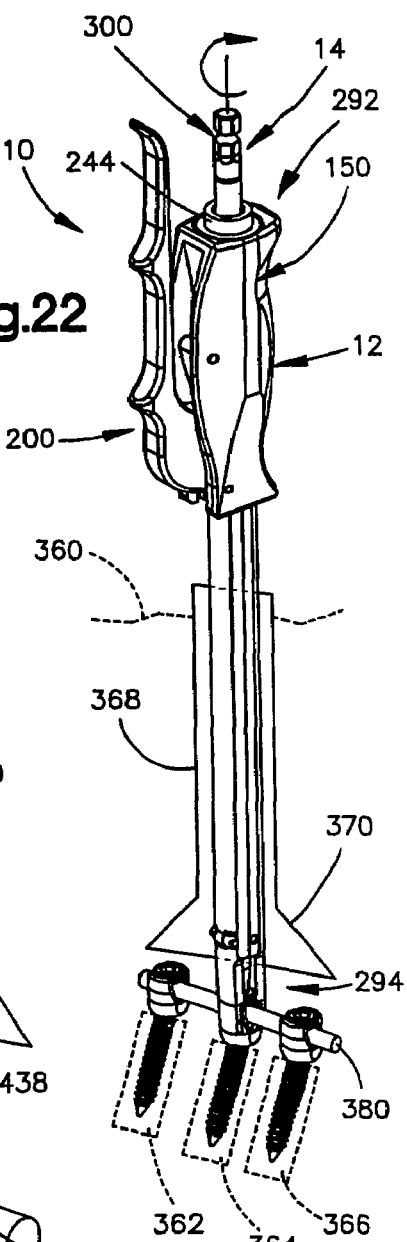

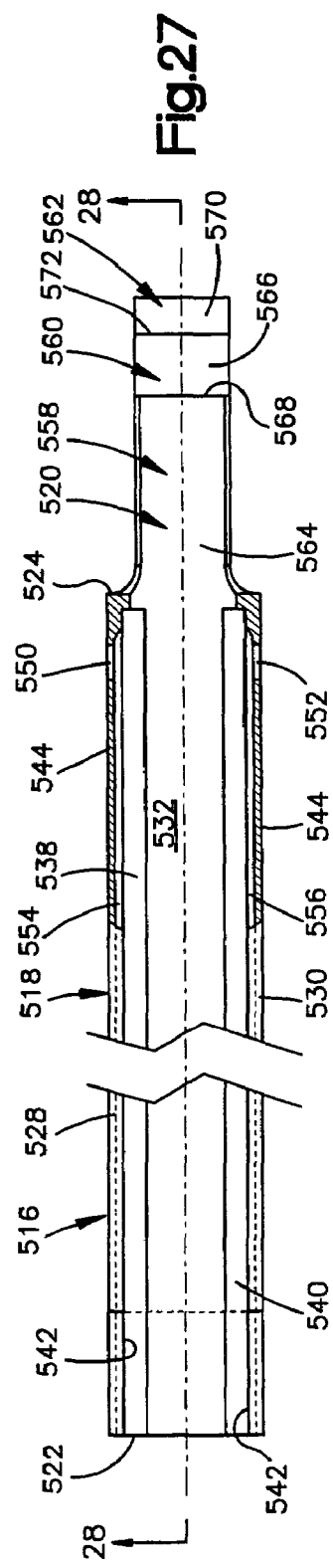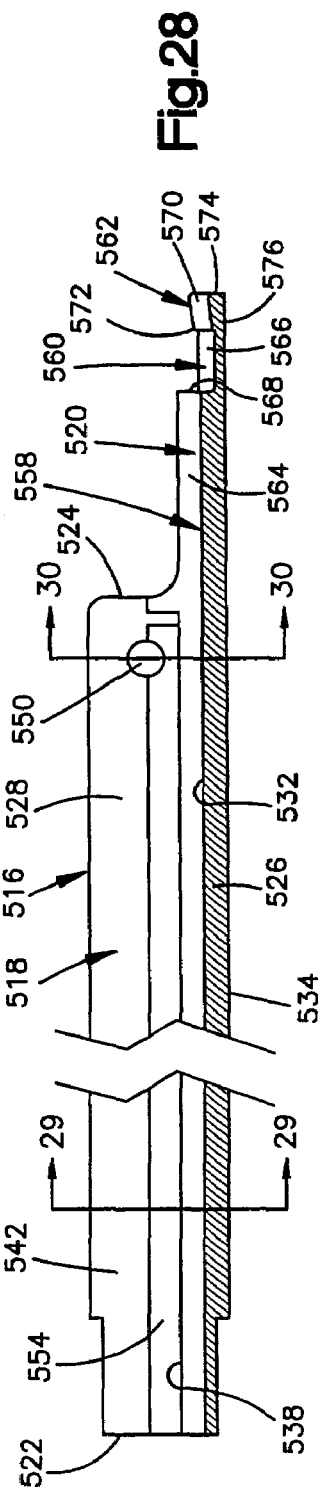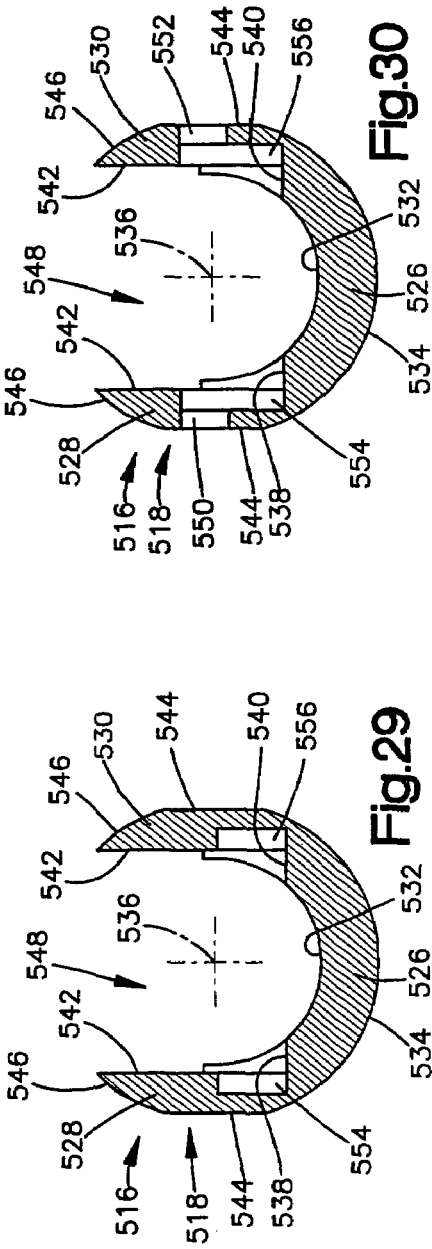

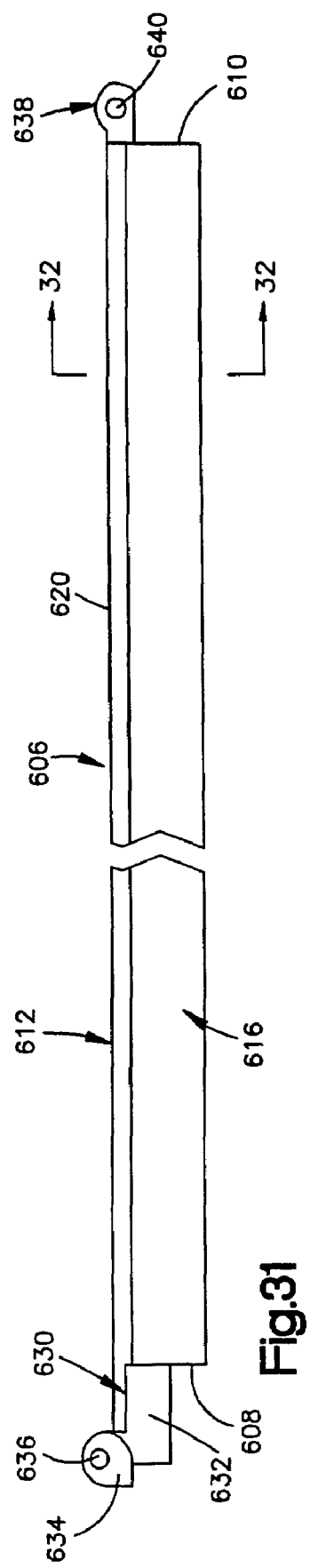
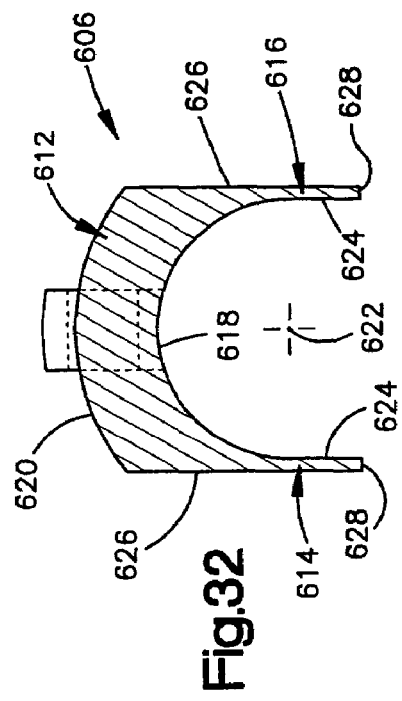
Fig.31
Fig.32

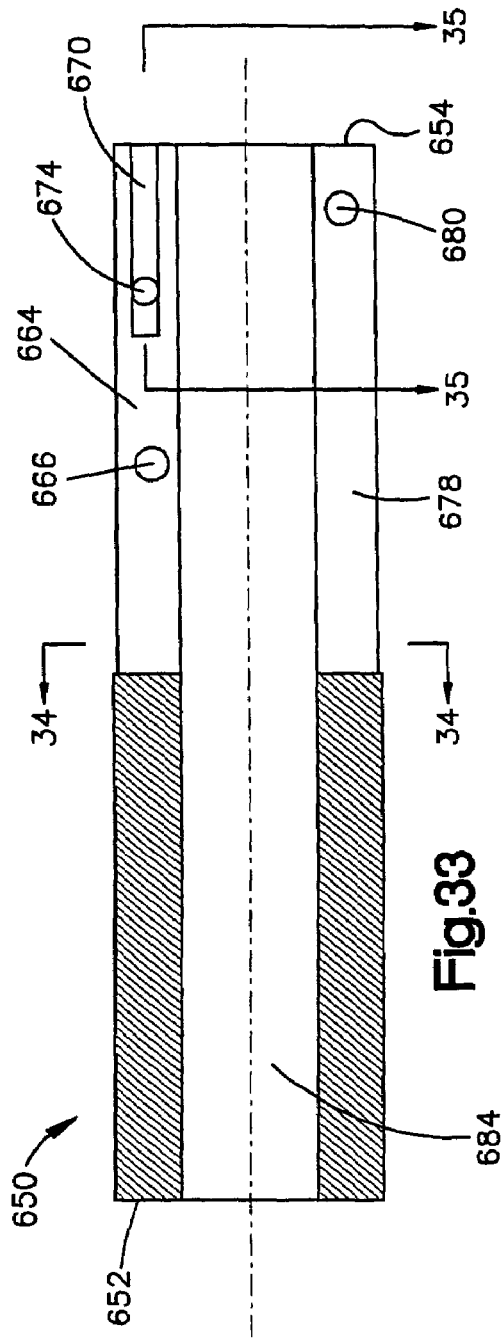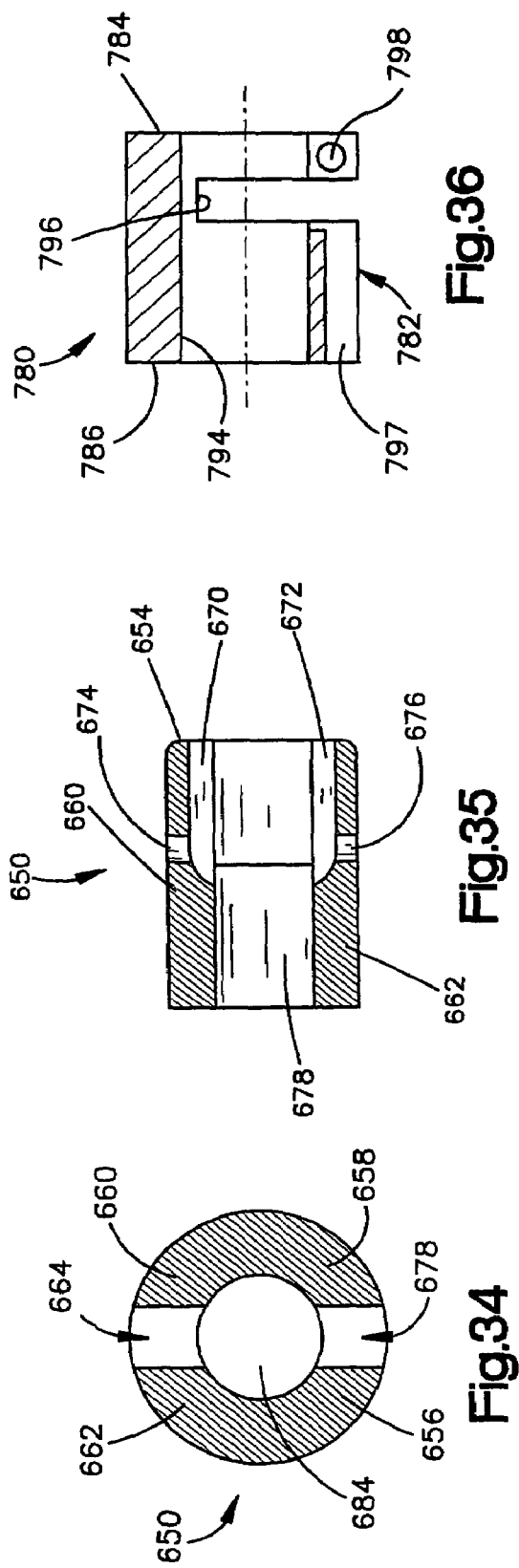

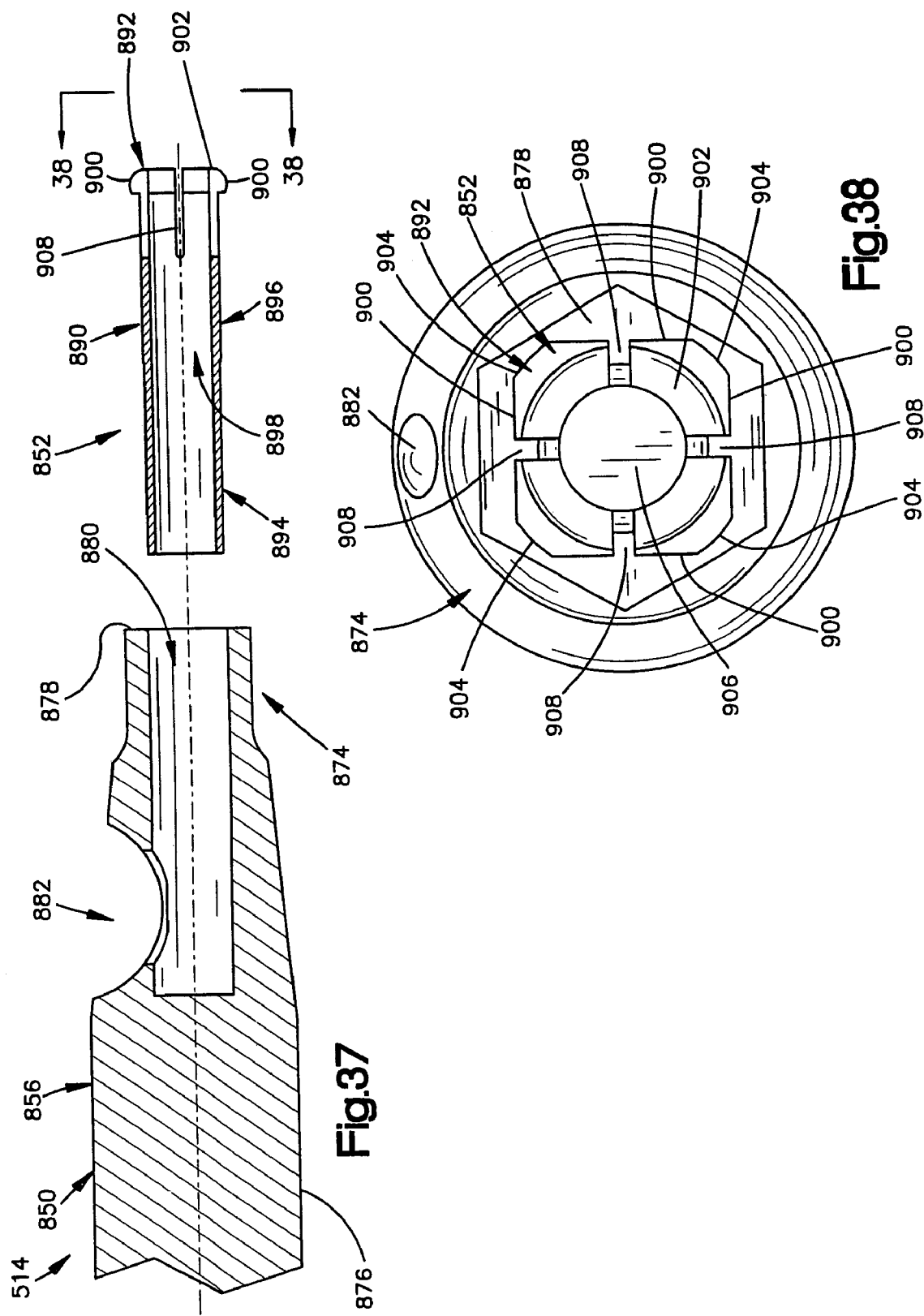

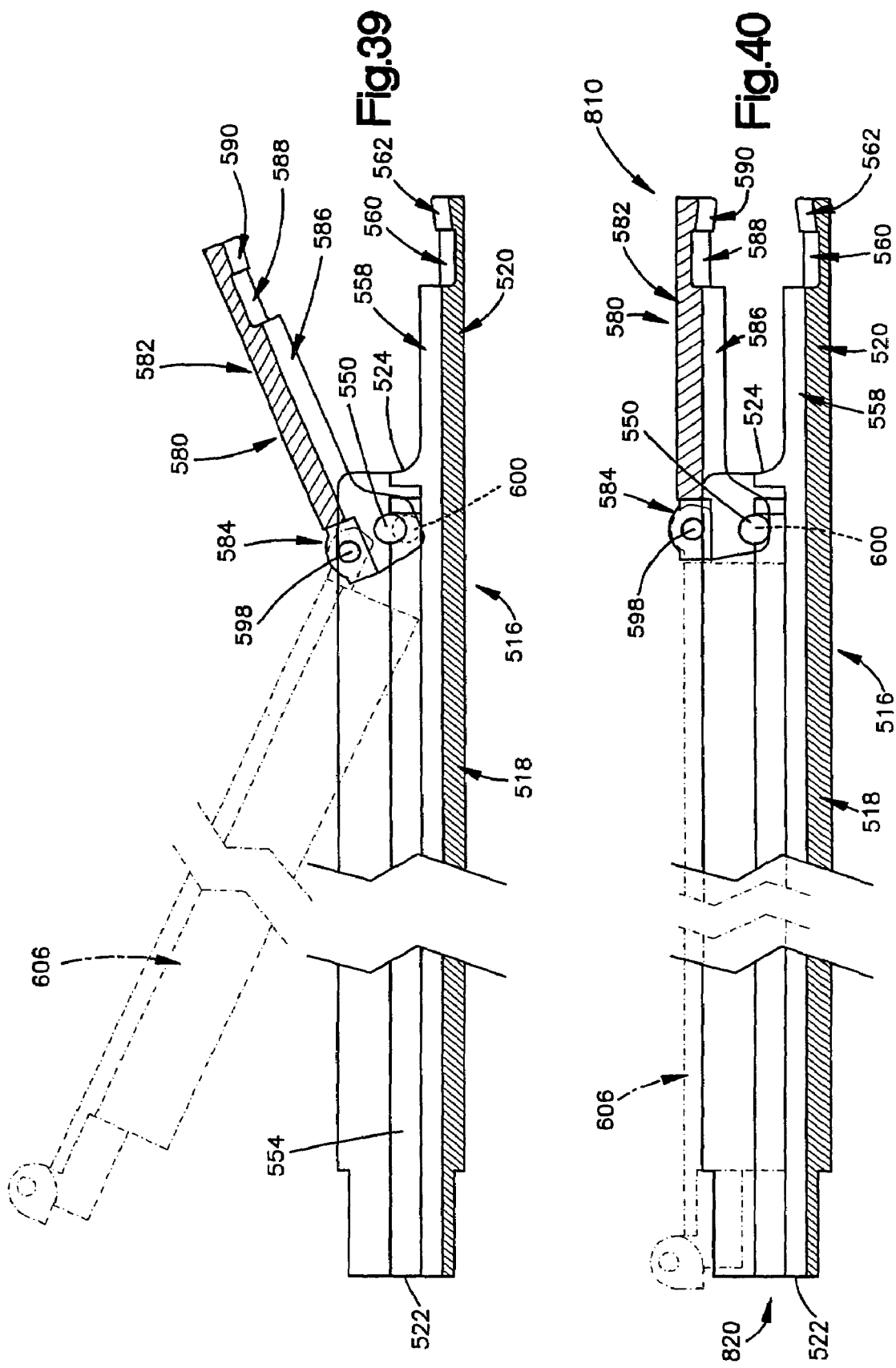

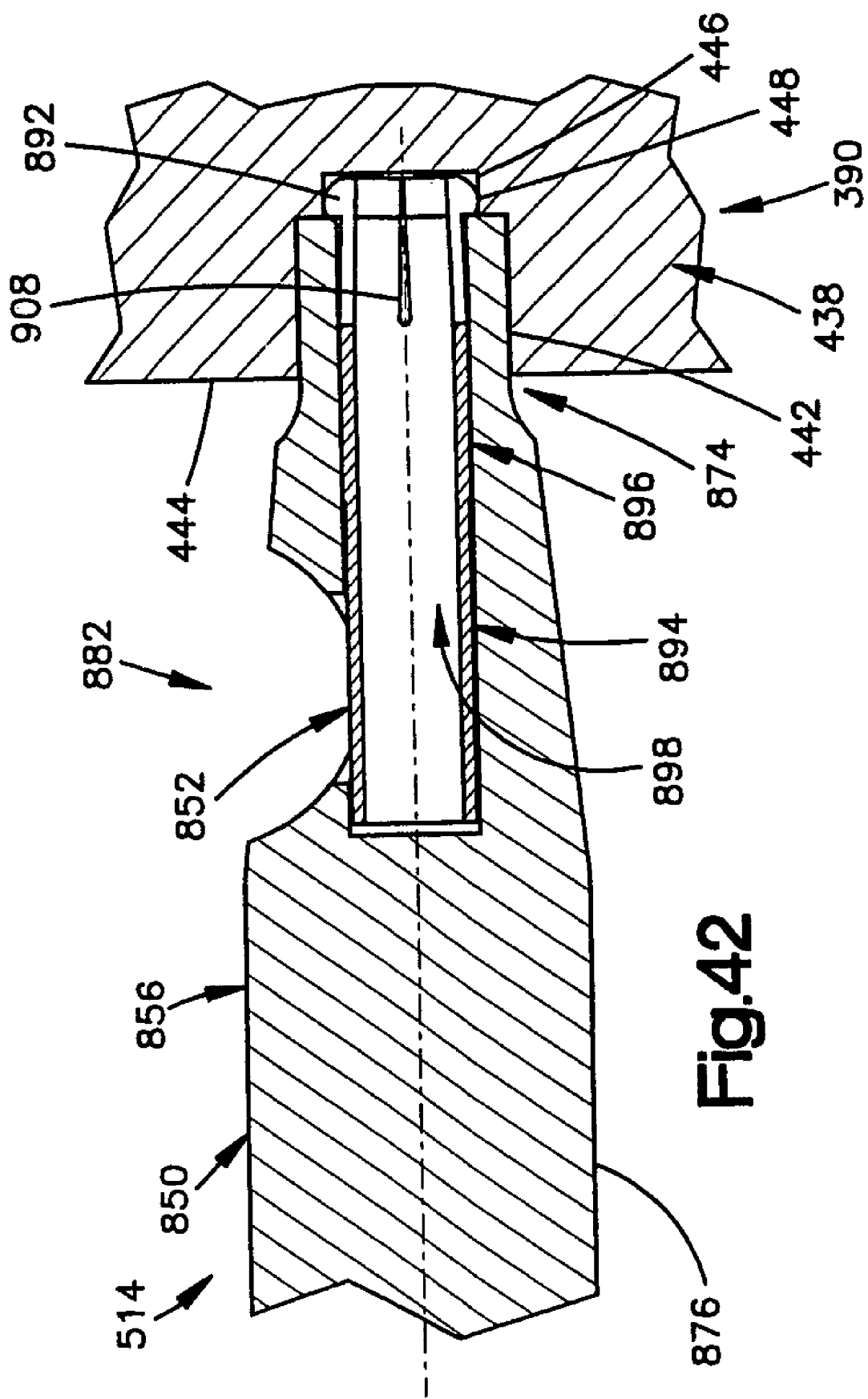

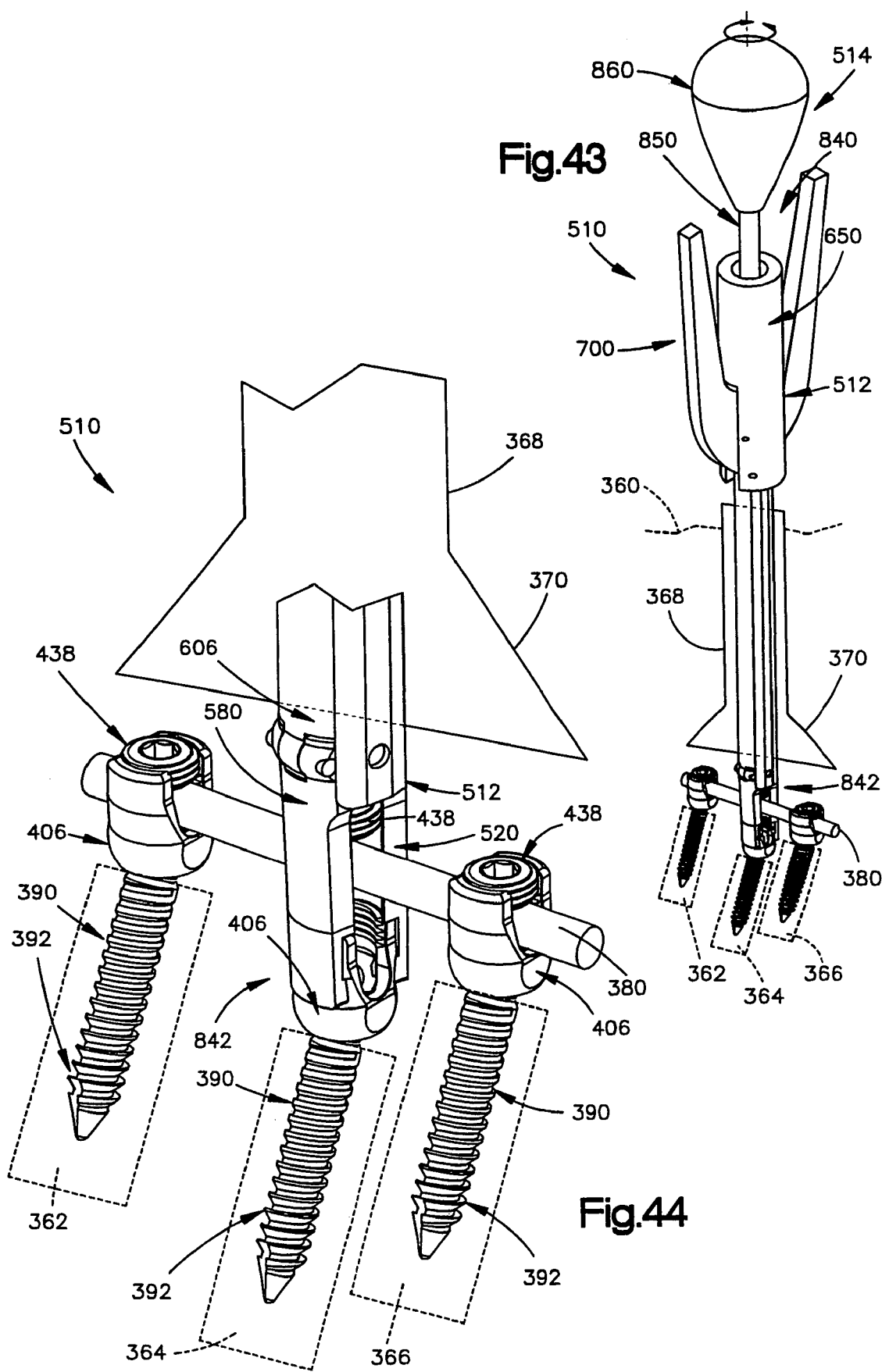

US 7,618,444 B2

SURGICAL INSTRUMENT FOR MOVING A VERTEBRA

RELATED APPLICATIONS

The present application is a continuation of International Patent Application No. PCT/US03/027879, filed Sep. 5, 2003, which is a continuation-in-part of U.S. patent application Ser. No. 10/236,713, filed Sep. 6, 2002, now U.S. Pat. No. 6,648,888. Both of these related applications are hereby incorporated herein by reference in their entirety.

TECHNICAL FIELD

The present inventions relate to a surgical instrument for moving a bone portion relative to another bone portion. More particularly, the present inventions relate to a surgical instrument for moving a vertebra relative to another vertebra.

BACKGROUND OF THE INVENTION

It is known to secure a fixation rod relative to a first vertebra for supporting a second vertebra that has moved away from, or slipped relative to, a desired position. An implant is attached to the second vertebra. The second vertebra is moved relative to the first vertebra so that the implant may be secured to the fixation rod.

A conventional surgical instrument for moving the second vertebra relative to the first vertebra for securing the implant to the fixation rod includes an instrument for attaching to the implant in the second vertebra. An outwardly extending flange of the instrument supports a corkscrew device. When supported in the flange, a distal end of the corkscrew device may be driven against the fixation rod. Rotation of the corkscrew device relative to the instrument drives the fixation rod into the implant in the second vertebra. An implant plug is introduced into the implant through a cannulation in the instrument. The implant plug secures the implant to the rod so that the second vertebra becomes fixed relative to the first vertebra.

SUMMARY OF THE INVENTION

The present invention relates to a surgical instrument for moving a first bone portion relative to a second bone portion. The surgical instrument includes a first device adapted to be connected to a fastener fixed to the first bone portion. The first device has a part movable in a direction away from the first bone portion when subjected to a predetermined load. A second device includes a first portion associated with the part of the first device. A second portion of the second device supports a member which engages the fastener fixed to the first bone portion and secures a rod connected to the second bone portion to the fastener. The second portion is adapted for pressing the member against the rod. The part is stationary relative to the first bone portion when a force necessary to produce relative movement between the first and second bone portions is below the predetermined load so that relative movement between the first and second devices moves the fastener that is fixed to the first bone portion and the first bone portion relative to the second bone portion and relative to the rod.

According to another aspect, the present invention relates to a surgical instrument for moving a first bone portion of a body relative to a second bone portion of the body. The surgical instrument includes a structure forming a passage into the body. A first device is extendable through the passage formed by the structure. The first device is adapted to be connected to a fastener fixed to the first bone portion. The first device has a part movable in a direction away from the first bone portion when subjected to a predetermined load. A second device is also extendable through the passage formed by the structure. The second device includes a first portion associated with the part of the first device. A second portion of the second device supports a member which engages the fastener fixed to the first bone portion and secures a rod connected to the second bone portion to the fastener. The second portion is adapted for pressing the member against the rod. The part is stationary relative to the first bone portion when a force necessary to produce relative movement between the first and second bone portions is below the predetermined load so that relative movement between the first and second devices moves the fasteners fixed to the first bone portion and the first bone portion relative to the second bone portion and relative to the rod.

According to yet another aspect, the present invention relates to a surgical instrument for threadedly connecting a member and a fastener. The surgical instrument includes a first device adapted to be connected to the fastener. A second device includes a first portion associated with the first device and a second portion for supporting the member to be threadedly connected to the fastener. The first device has a part that prevents the second device from moving toward the fastener that is connected to the first device so that the member is rotated relative to the fastener but is not moved axially relative to the fastener in response to rotation of the second device.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2 is a top plan view of a fixed shaft of a reduction device of the surgical instrument of FIG. 1;

FIG. 3 is a view taken along line 3-3 in FIG. 2;

FIG. 4 is a view taken along line 4-4 in FIG. 3;

FIG. 5 is a view taken along line 5-5 in FIG. 3;

FIG. 6 is an elevation view of an actuator shaft of the reduction device of the surgical instrument of FIG. 1;

FIG. 7 is a view taken along line 7-7 in FIG. 6;

FIG. 8 is a cross-sectional view of a fixed handle of the reduction device of the surgical instrument of FIG. 1;

FIG. 9 is a view taken along line 9-9 in FIG. 8;

FIG. 10 is a view taken along line 10-10 in FIG. 8;

FIG. 12 is an enlarged view of a driver spring and a second axial end of a driver of a drive device of the surgical instrument of FIG. 1;

FIG. 13 is a view taken along line 13-13 in FIG. 12;

FIG. 14 is a view illustrating the assembly of a pivotal jaw to the fixed shaft of the reduction device of the surgical instrument of FIG. 1;

FIG. 15 is a view illustrating the pivotal jaw attached to the fixed shaft of the reduction device of the surgical instrument of FIG. 1;

FIG. 16 is a side view, partially in section, of the surgical instrument of FIG. 1;

FIG. 22 illustrates the surgical instrument of FIG. 1 inserting a setscrew into the fastener of FIG. 17 to secure a vertebra to a rod;

FIG. 23 is an enlarged portion of FIG. 22;

FIG. 27 is a top plan view of a fixed shaft of a reduction device of the surgical instrument of FIG. 26;

FIG. 28 is a view taken along line 28-28 in FIG. 27;

FIG. 29 is a view taken along line 29-29 in FIG. 28;

FIG. 30 is a view taken along line 30-30 in FIG. 28;

FIG. 31 is an elevation view of an actuator shaft of the reduction device of the surgical instrument of FIG. 26;

FIG. 32 is a view taken along line 32-32 in FIG. 31;

FIG. 33 is a cross-sectional view of a fixed handle of the reduction device of the surgical instrument of FIG. 26;

FIG. 34 is a view taken along line 34-34 in FIG. 33;

FIG. 35 is a view taken along line 35-35 in FIG. 33;

FIG. 36 is a cross-sectional view of a translation mechanism of the reduction device of the surgical instrument of FIG. 26;

FIG. 37 is an enlarged view of a driver spring and a second axial end of a driver of a drive device of the surgical instrument of FIG. 26;

FIG. 38 is a view taken along line 38-38 in FIG. 37;

FIG. 39 is a view illustrating the assembly of a pivotal jaw to the fixed shaft of the reduction device of the surgical instrument of FIG. 26;

FIG. 40 is a view illustrating the pivotal jaw attached to the fixed shaft of the reduction device of the surgical instrument of FIG. 26;

FIG. 42 illustrates a setscrew held on the second axial end of the drive device of the surgical instrument of FIG. 26;

FIG. 43 illustrates the surgical instrument of FIG. 26 being used to move a vertebra;

FIG. 44 is an enlarged portion of FIG. 43;

DETAILED DESCRIPTION OF THE PREFERRED EMBODIMENT

Figure 1:
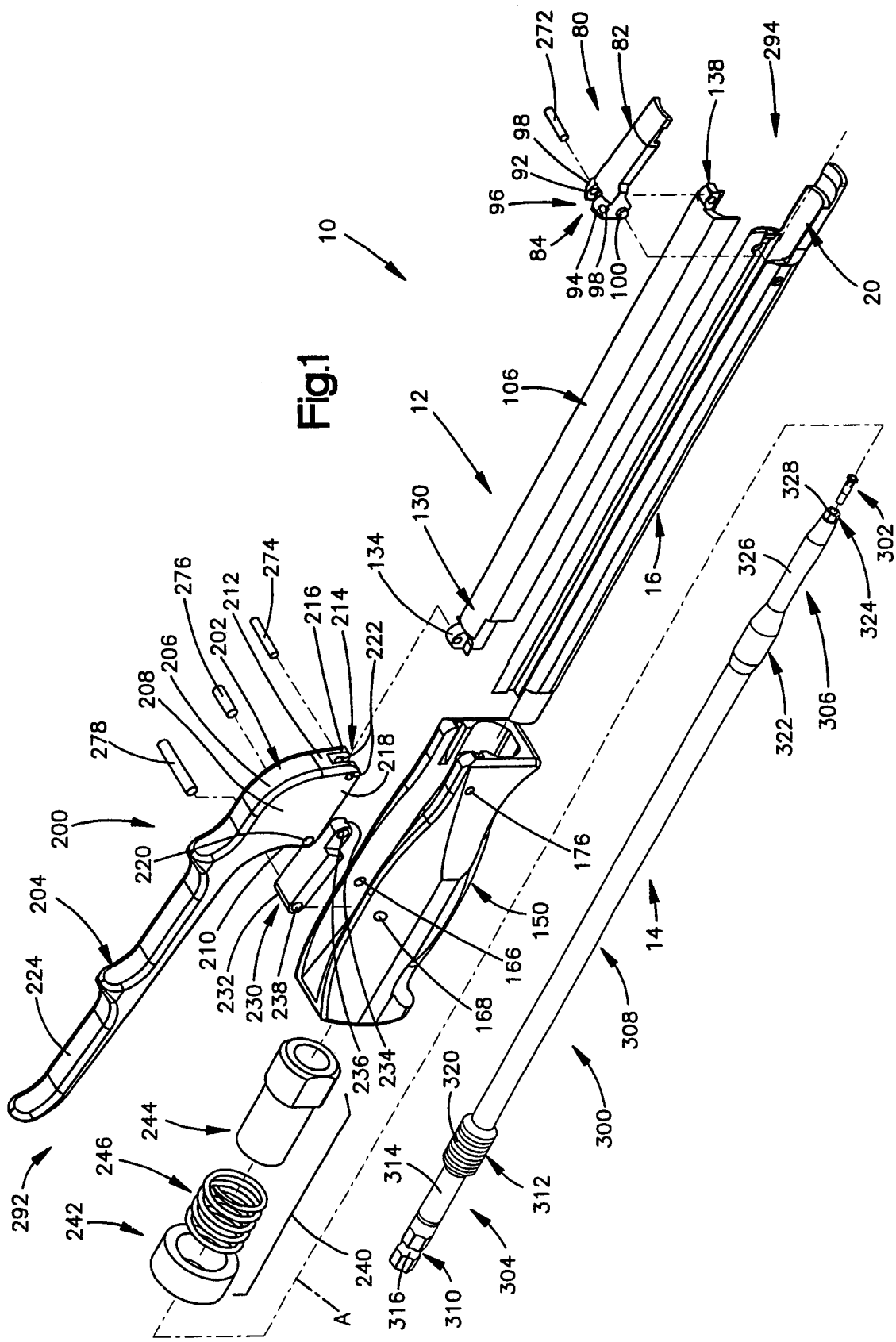
FIG. 1 is an exploded, perspective view of a surgical instrument constructed in accordance with the present invention.

FIG. 1 is an exploded perspective view of a surgical instrument 10 constructed in accordance with the present invention. The surgical instrument 10 includes a reduction device 12 and a drive device 14.

The reduction device 12 includes a fixed shaft 16 that is formed from a biocompatible material. As shown in FIGS. 2-3, the fixed shaft 16 includes a main body portion 18 and a fixed jaw 20. The main body portion 18 extends axially between first and second axial ends 22 and 24, respectively. The main body portion 18 has a generally C-shaped cross-section, as shown in FIGS. 4-5. A bottom wall 26 and opposite first and second side walls 28 and 30, respectively, define the C-shaped cross-section of the main body portion 18 of the fixed shaft 16. The bottom wall 26 is arced and includes arcuate inner and outer surfaces 32 and 34, respectively. The inner surface 32 of the bottom wall 26 is centered at point 36. The bottom wall 26 terminates at first and second end surfaces 38 and 40, respectively. An arc length of the bottom wall of the fixed shaft is less than 180 degrees about point 36.

The first and second side walls 28 and 30 of the main body portion 18 of the fixed shaft 16 extend upwardly from the first and second end surfaces 38 and 40, respectively. The first and second side walls 28 and 30 include planar inner and outer surfaces 42 and 44, respectively, that are connected by curved end surfaces 46. The inner surface 42 of the first side wall 28 extends upwardly from a lateral midpoint of the first end surface 38 of the bottom wall 26 in a direction perpendicular to the first end surface 38. The outer surface 44 of the first side wall 28 extends parallel to the inner surface 42 and is contiguous with the outer surface 34 of the bottom wall 26. The inner surface 42 of the second side wall 30 extends upwardly from a lateral midpoint of the second end surface 40 of the bottom wall 26 in a direction perpendicular to the second end surface 40 of the bottom wall 26. The outer surface 44 of the second side wall 30 extends parallel to the inner surface 42 and is contiguous with the outer surface 34 of the bottom wall 26.

The arcuate inner surface 32 of the bottom wall 26 and the parallel inner surfaces 42 of the first and second side walls 28 and 30 collectively define a channel 48 (FIG. 4) in the main body portion 18 of the fixed shaft 16. An open top of the fixed shaft 16 leads into the channel 48.

First and second coaxial through-holes 50 and 52, respectively, extend through the first and second side walls 28 and 30, respectively, adjacent the second axial end 24 of the main body portion 18 of the fixed shaft 16. The centers of the first and second through-holes 50 and 52 are aligned with point 36.

A slot 54 extends into the inner surface 42 of the first side wall 28 of the main body portion 18 of the fixed shaft 16 adjacent the first end surface 38 of the bottom wall 26. As shown in FIG. 3, the slot 54 in the first side wall 28 extends from the first axial end 22 of the main body portion 18 and terminates adjacent the first through-hole 50 near the second axial end 24 of the main body portion 18. The slot 54 is open on the first axial end 22 and is closed on the second axial end 24. The slot 54 partially intersects a lower portion of the first through-hole 50.

A slot 56 extends into the inner surface 42 of the second side wall 30 of the main body portion 18 adjacent the second end surface 40 of the bottom wall 26. As shown in FIG. 2, the slot 56 in the second side wall 30 extends from the first axial end 22 of the main body portion 18 and terminates adjacent the second through-hole 52 near the second axial end 24 of the main body portion 18. The slot 56 is open on the first axial end 22 and is closed on the second axial end 24. As shown in FIG. 2, the slot 56 partially intersects a lower portion of the second through-hole 52.

The fixed jaw 20 of the fixed shaft 16 extends axially outwardly of the bottom wall 26 of the main body portion 18 of the fixed shaft 16. The fixed jaw 20 includes a linking portion 58, a mouth portion 60 and a gripping portion 62.

As shown in FIGS. 2-3, an inner surface 64 of the linking portion 58 is arcuate and is formed by an axial extension of the inner surface 32 of the bottom wall 26. The mouth portion 60 of the fixed jaw 20 includes an arcuate inner surface 66. A shoulder 68 connects the inner surface 66 of the mouth portion 60 to the inner surface 64 of the linking portion 58. The gripping portion 62 includes a tapered inner surface 70. A shoulder 72 connects the inner surface 66 of the mouth portion 60 to the tapered inner surface 70 of the gripping portion 62. The tapered inner surface 70 of the gripping portion 62 widens near a terminal end 74 (FIG. 3) of the fixed jaw 20. An outer surface 76 of the fixed jaw 20 is arcuate. As shown in FIG. 3, the inner surface 66 of the mouth portion 60 is recessed, or nearer the outer surface 76 of the fixed jaw 20, relative to the inner surfaces 64 and 70 of the linking portion 58 and the gripping portion 62.

The reduction device 12 also includes a pivotal jaw 80 (FIG. 1). The pivotal jaw 80 includes a main body portion 82 and a pivotal portion 84. The main body portion 82 of the pivotal jaw 80 is a mirror image of the fixed jaw 20 of the fixed shaft 16. The pivotal jaw 80 also includes a linking portion 86, a mouth portion 88, and a gripping portion 90.

As shown in FIG. 1, the pivotal portion 84 of the pivotal jaw 80 includes first and second members 92 and 94, respectively, that are separated from one another by a central channel 96. Laterally extending through-holes 98 extend through an upper portion of the first and second members 92 and 94. A cylindrical pivot element 100 extends laterally outwardly of a lower portion of each of the first and second members 92 and 94.

The reduction device 12 also includes an actuator shaft 106, shown in detail in FIGS. 6-7. The actuator shaft 106 extends axially between first and second axial ends 108 and 110, respectively. An arcuate upper wall 112 and parallel side walls 114 and 116 define a generally C-shaped cross-section of the actuator shaft 106. The arcuate upper wall 112 includes inner and outer surfaces 118 and 120, respectively. The outer surface 120 of the upper wall 112 has a larger radius of curvature than the inner surface 118. The inner surface 118 is centered on point 122.

The side walls 114 and 116 of the actuator shaft 106 extend downwardly from the upper wall 112 beyond point 122. Each side wall 114 and 116 includes parallel inner and outer surfaces 124 and 126, respectively, and terminates at a lower end surface 128. The actuator shaft 106 has a width, measured laterally between the outer surfaces 126 of the side walls 114 and 116, that is sized to fit within the channel 48 of the fixed shaft 16 so that each side wall 114 and 116 of the actuator shaft 106 extends adjacent an associated side wall 28 and 30 of the fixed shaft 16.

A first linking element 130 of the actuator shaft 106 extends axially outwardly of the first axial end 108 of the actuator shaft 106. The first linking element 130 includes an axial extension 132 and a linking member 134. The axial extension 132 extends axially outwardly of the first axial end 108 of the actuator shaft 106 and supports the linking member 134.

The linking member 134 extends axially outwardly of the axial extension 132. A laterally extending through-hole 136 extends through the linking member 134.

A second linking element 138 extends axially outwardly of the second axial end 110 of the actuator shaft 106. A laterally extending through-hole 140 extends through the second linking element 138.

FIGS. 8-10 illustrate a fixed handle 150 of the reduction device 12. An axial length of the fixed handle 150 is defined between first and second axial ends 152 and 154, respectively. An outer surface 156 of the fixed handle 150 has a contour for receiving the palm of a hand. The outer surface 156 is defined by a curvilinear bottom wall 158 and opposite, arcuate side walls 160 and 162. An upper portion of the fixed handle 150, opposite the bottom wall 158, includes an axially extending channel 164 (FIG. 9), which is open at the top. A width of the channel 164 is defined between upper portions of the side walls 160 and 162 of the fixed handle 150.

First and second through-holes 166 and 168, respectively, (FIG. 1) extend through the upper portions of the side walls 160 and 162 to connect to the channel 164. The first and second through-holes 166 and 168 are located away from the first axial end 152 of the fixed handle 150 by approximately forty percent of the axial length of the fixed handle 150. The first and second through-holes 166 and 168 are coaxial with one another.

First and second axially extending slots 170 and 172 (FIG. 10), each of which is open to channel 164, extend into the upper portions of the side walls 160 and 162 adjacent the second axial end 154 of the fixed handle 150. Each of the first and second slots 170 and 172 is located radially inwardly, relative to axis A, from the first and second through-holes 166 and 168. As shown in FIGS. 8 and 10, the first slot 170 extends axially along the upper portion of the side wall 160 over an axial length of approximately fifteen percent of the fixed handle 150 before terminating. A through-hole 174 extends through the upper portion of the side wall 160 and intersects the first slot 170. As shown in FIG. 10, the second slot 172 extends axially along the upper portion of the side wall 162 over an axial length of approximately fifteen percent of the fixed handle 150 before terminating. A through-hole 176 extends through the upper portion of the side wall 162 and intersects the second slot 172.

A bore 178 extends axially through the fixed handle 150 from the first axial end 152 to the second axial end 154. The bore 178 includes a widened portion 180 (FIG. 8) adjacent the second axial end 154 of the fixed handle 150 for forming a seat for receiving the first axial end 22 of the main body portion 18 of the fixed shaft 16. The bore 178 widens into a series of wider diameter bores adjacent the first axial end 152 of the fixed handle 150. The series of wider diameter bores includes a first cylindrical bore 182, a second cylindrical bore 184, and a non-cylindrical bore 186.

The first cylindrical bore 182 is located immediately adjacent the first axial end 152 of the fixed handle 150. A cylindrical surface 188 that defines the first cylindrical bore 182 is threaded. The second cylindrical bore 184 is located immediately adjacent the first cylindrical bore 182 and has a smaller diameter than the first cylindrical bore 182. A cylindrical surface 190 defines the second cylindrical bore 184. The non-cylindrical bore 186 is located immediately adjacent the second cylindrical bore 184, opposite the first cylindrical bore 182. FIG. 9 is a cross-sectional view of the fixed handle 150 illustrating the non-cylindrical bore 186. The non-cylindrical bore 186 has an oblong shape that is defined by arcuate upper and lower surfaces 192 and 194, respectively, that are interconnected by parallel, planar surfaces 196 and 198. The planar surfaces 196 and 198 define a narrow portion of the oblong shaped non-cylindrical bore 186.

An actuation handle 200 (FIG. 1) of the reduction device 12 includes a main body portion 202 and an axially extending actuator portion 204. The main body portion 202 of the actuator handle 200 includes a rounded upper surface 206, a bottom surface (not shown), and planar first and second side surfaces 208. Only the second side surface 208 is shown in FIG. 1. The rounded upper surface 206 of the actuator handle 200 also includes first and second axial ends 210 and 212, respectively.

An axially extending channel 214 extends into the bottom surface of the actuator handle 200 to define first and second flanges 216 and 218, respectively. The first flange 216 extends between the first and second axial ends 210 and 212 of the main body portion 202 adjacent the first side surface. The second flange 218 extends between the first and second axial ends 210 and 212 of the main body portion 202 adjacent the second side surface 208. Coaxial through-holes 220 (only one of which is shown) extend through the first and second flanges 216 and 218 adjacent the first axial end 210 of the main body portion 202. Coaxial through-holes 222 extend through the first and second flanges 216 and 218 adjacent the second axial end 212 of the main body portion 202.

The actuator portion 204 of the actuator handle 200 extends axially outwardly of the first axial end 210 of the main body portion 202. The actuator portion 204 is an elongated rod having gripping features located on an upper surface 224.

An actuator linkage 230 (FIG. 1) of the reduction device 12 has a generally rectangular shape that is defined between first and second axial ends 232 and 234, respectively. Cutouts are removed from the second axial end 234 of the actuator linkage 230 so that a narrowed portion remains. A first through-hole 236 extends laterally through the narrowed portion of the actuator linkage 230 adjacent the second axial end 234. A second through-hole 238 extends laterally through the actuator linkage adjacent the first axial end 232.

Figure 11:
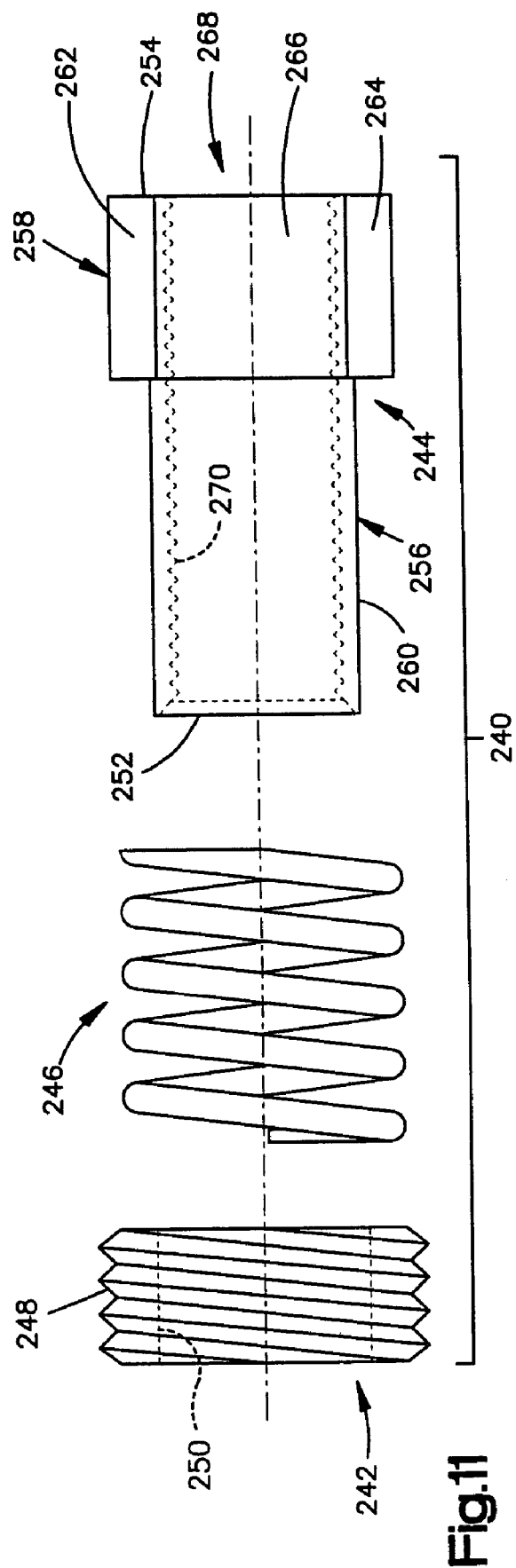
FIG. 11 is an exploded view of a translation mechanism of the reduction device of the surgical instrument of FIG. 1.

The reduction device 12 also includes a translating mechanism 240. FIG. 11 shows an exploded side view of the translating mechanism 240. The translating mechanism 240 includes a locking cap 242, a part or carriage 244, and a spring 246.

The locking cap 242 is tubular and includes a threaded outer surface 248. The threaded outer surface 248 is sized to thread into the first cylindrical bore 182 of the fixed handle 150. An inner surface 250, shown by dashed lines in FIG. 11, of the locking cap 242 defines a bore having a diameter that is greater than the diameter of the bore 178 extending through the fixed handle 150.

The part or carriage 244 extends axially between first and second axial ends 252 and 254, respectively and includes a slider portion 256 and a head portion 258. The slider portion 256 extends from the first axial end 252 of the part or carriage 244 and has a cylindrical outer surface 260 that is dimensioned to be received in the bore of the locking cap 242. The head portion 258 extends from the second axial end 254 of the carriage 244 and has an oblong outer surface that includes arcuate upper and lower surfaces 262 and 264, respectively, that are connected by parallel, planar surfaces 266 (only one of which is shown). The head portion 258 of the carriage 244 is dimensioned to be received in the non-cylindrical bore 186 of the fixed handle 150 so that the planar surfaces 266 of the head portion 258 of the carriage 244 lie adjacent the planar surfaces 196 and 198 that define the non-cylindrical bore 186.

An axially extending bore 268 extends through the carriage 244 between the first and second axial ends 252 and 254. A threaded surface 270, shown by dashed lines in FIG. 11, defines the bore 268.

The spring 246 of the translating mechanism 240 urges the carriage 244 away from the locking cap 242. The spring 246 illustrated in FIG. 11 is a helical spring. The spring 246 has a predetermined spring constant. An inner diameter of the spring 246 is greater than the outer diameter of the slider portion 256 of the part or carriage 244. An outer diameter of the spring 246 is less than the diameter between the arcuate upper and lower surfaces 262 and 264 of the head portion 258 of the carriage 244 and is greater than the diameter of the inner surface 250 of the locking cap 242.

To assemble the reduction device 12, the second linking element 138 of the actuator shaft 106 is inserted into the central channel 96 of the pivotal portion 84 of the pivotal jaw 80 and the through-hole 140 in the second linking element 138 is aligned with the through-holes 98 in the first and second members 92 and 94 of the pivotal portion 84 of the pivotal jaw 80. A pivot pin 272 (FIG. 1) is inserted through the aligned through-holes 98 and 140 and is secured to the first and second members 92 and 94 of the pivotal portion 84 of the pivotal jaw 80. The pivot pin 272 enables the pivotal jaw 80 to pivot relative to the actuator shaft 106.

Next, each of the pivot elements 100 of the pivotal jaw 80 is inserted into the opening of a respective slot 54 and 56 that is open on the first axial end 22 of the fixed shaft 16. With the actuator shaft 106 angled upwardly away from the fixed shaft 16, as shown in FIG. 14, the pivotal jaw 80 is moved toward the second axial end 24 of the fixed shaft 16. The pivotal jaw 80 is moved into the position shown in FIG. 14 in which each of the pivot elements 100 is located adjacent the through-hole 50 and 52 of the slot 54 and 56, respectively, near the second axial end 24 of the fixed shaft 16. The first axial end 22 of the fixed shaft 16 is then inserted into the widened portion 180 of the fixed handle 150 and the fixed shaft 16 is secured, for example by welding, to the fixed handle 150. After securing the fixed shaft 16 to the fixed handle 150, the actuator shaft 106 is moved downwardly from the position shown in FIG. 14 to the position shown in FIG. 15. During the downward movement of the actuator shaft 106, the pivotal jaw 80 is forced upwardly so that the pivot elements 100 of the pivotal jaw 80 become located in the through-holes 50 and 52. When located in the through-holes 50 and 52, the pivot elements 100 of the pivotal jaw 80 are prevented from moving axially relative to the fixed shaft 16. The pivotal jaw 80 and the fixed jaw 20, when connected together as shown in FIG. 15, collectively form a clamp 280.

The actuator shaft 106, when moved downwardly into the position shown in FIG. 15, is received within the channel 48 of the fixed shaft 16. When received in the channel 48 of the fixed shaft 16, the end surfaces 128 of the side walls 114 and 116 of the actuator shaft 106 rest on the first and second end surfaces 38 and 40 of the bottom wall 26 of the fixed shaft 16. The outer surfaces 126 of the side walls 114 and 116 of the actuator shaft 106 lie in the channel 48 of the fixed shaft 16 adjacent the inner surfaces 42 of the first and second side walls 28 and 30 of the fixed shaft 16. When the actuator shaft 106 is lying adjacent the fixed shaft 16 as shown in FIG. 15, the point 122 of the actuator shaft 106 and the point 36 of the fixed shaft 16 align on a central axis of a cylindrical passage 290 that is formed between the actuator shaft 106 and the fixed shaft 20.

When the actuator shaft 106 is moved downwardly into the channel 48 of the fixed shaft 16, the first linking element 130 of the actuator shaft 106 is received in the channel 164 of the fixed handle 150. The actuator shaft 106 is moved axially to align the through-hole 136 in the linking member 134 of the first linking element 130 with the through-holes 174 and 176 extending into the slots 170 and 172 in the fixed handle 150. The actuator handle 200 is then inserted into the channel 164 in the fixed handle 150 so that the linking member 134 of the first linking element 130 of the actuator shaft 106 is received in the channel 214 between the first and second flanges 216 and 218 of the actuator handle 200. The actuator handle 200 is moved to align the coaxial through-holes 222 adjacent the second axial end 212 of the actuator handle 200 with the through-hole 136 in the linking member 134 of the first linking element 130 of the actuator shaft 106 and the through-holes 174 and 176 of the fixed handle 150. A pivot pin 274 (FIG. 1) is then inserted through one of the through-holes 174 and 176 in the fixed handle 150 and into the though-holes 222 and 136 in the actuator handle 200 and the first linking element 130, respectively. When properly inserted, one end of the pivot pin 274 is located in the slot 170 of the side wall 160 of the fixed handle 150 and the other end of the pivot pin 274 is located in the slot 172 of the side wall 162 of the fixed handle 150. A center portion of the pivot pin 274 enables pivotal movement of the actuator handle 200 relative to the actuator shaft 106 about the pivot pin 274 while the ends of the pivot pin 274 are retained within the slots 170 and 172 of the fixed handle 150.

The second axial end 234 of the actuator linkage 230 is then inserted into the channel 214 of the actuator handle 200 and the through-hole 236 of the second axial end 234 of the actuator linkage 230 is aligned with the coaxial through-holes 220 adjacent the first axial end 210 of the actuator handle 200. A pivot pin 276 (FIG. 1) is inserted into the aligned through-holes 236 and 220 and is secured to the first and second flanges 216 and 218 of the actuator handle 200. The pivot pin 276 enables pivotal movement between the actuator linkage 230 and the actuator handle 200.

The through-hole 238 in the first axial end 232 of the actuator linkage 230 is then aligned with the through-holes 166 and 168 in the upper portions of the side walls 160 and 162 of the fixed handle 150. A pivot pin 278 (FIG. 1) is inserted into the aligned through-holes 238, 166, and 168 and is secured to the upper portions of the side walls 160 and 162 of the fixed handle 150. The pivot pin 278 enables pivotal movement of the actuator linkage 230 relative to the fixed handle 150 for opening and closing the clamp 280 of the reduction device 12.

Figure 21:
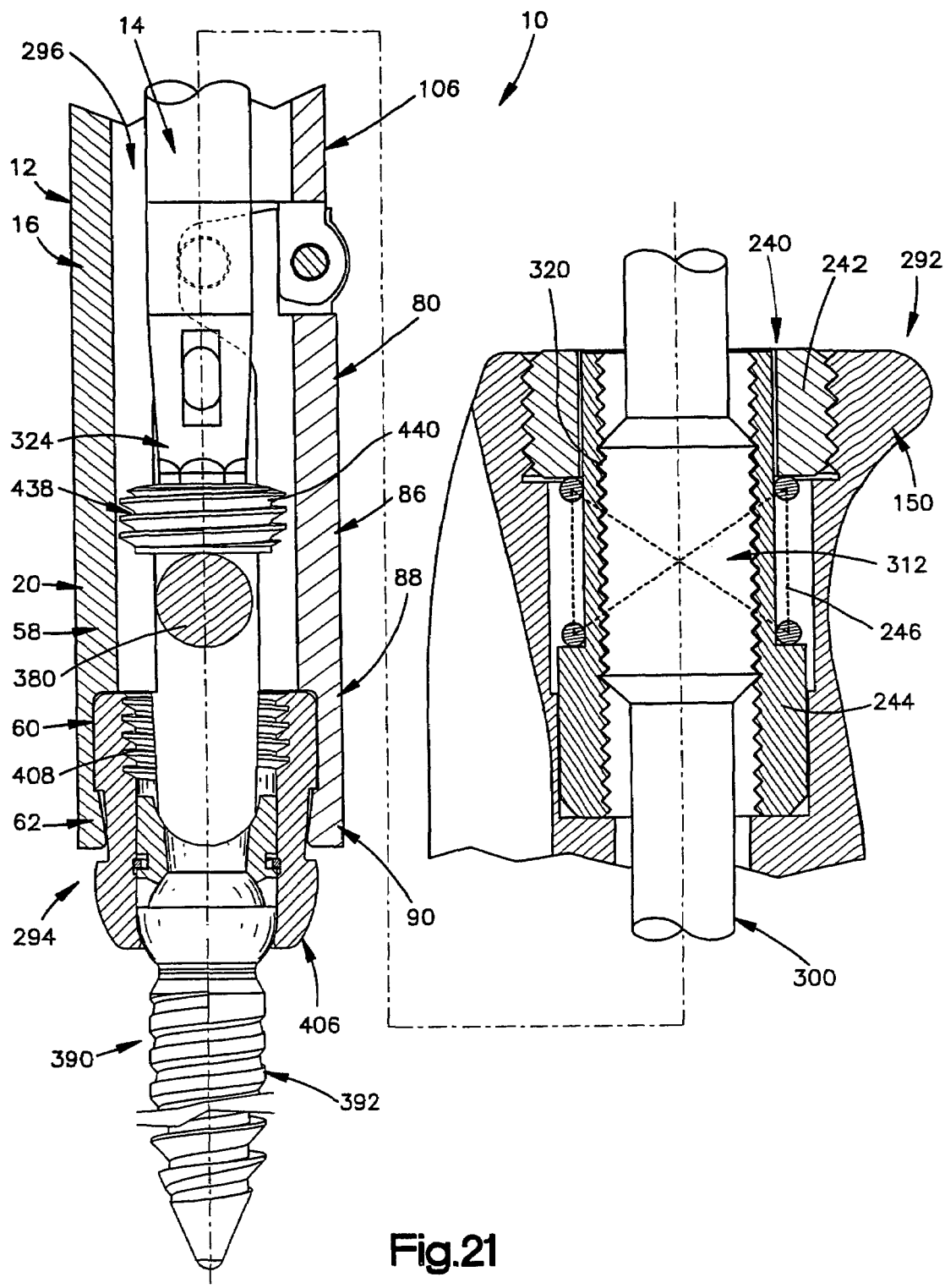
FIG. 21 illustrates a cross-sectional view of a portion of the surgical instrument of FIG. 1 being used in conjunction with the fastener of FIG. 21.

The translating mechanism 240 is then assembled into the fixed handle 150. To assemble the translating mechanism 240 in the fixed handle 150, the part or carriage 244 is inserted, head portion 258 first, through the first and second cylindrical bores 182, and 184 adjacent the first axial end 152 of the fixed handle 150 and into the non-cylindrical bore 186. When the head portion 258 of the carriage 244 is located in the non-cylindrical bore 186, the interaction between the planar surfaces 266 of the head portion 258 of the carriage 244 and the planar surfaces 196 and 198 defining the non-cylindrical bore 186 prevent the carriage 244 from rotating relative to the fixed handle 150. When the head portion 258 of the carriage 244 is located in the non-cylindrical bore 186, the slider portion 256 of the carriage 244 extends through the second cylindrical bore 184 and at least partially through the first cylindrical bore 182. FIG. 21 illustrates the slider portion 256 extending completely through the first cylindrical bore 182 to a position adjacent the first axial end 152 of the fixed handle 150.

The spring 246 is then placed around the slider portion 256 of the carriage 244 and is moved into contact with the head portion 258 of the carriage 244. The locking cap 242 is then screwed into the first cylindrical bore 182 and is locked in place with a substance such as LOCTITE®. When screwed into the first cylindrical bore 182, the locking cap 242 compresses the spring 246 to urge the carriage 244 to an end of the non-cylindrical bore 186 opposite the first axial end 152 of the fixed handle 150. The compressed spring 246 applies a predetermined axial load against the carriage 244 to prevent axial movement, or translation, of the carriage 244 toward the first axial end 152 of the fixed handle 150.

The assembled reduction device 12 includes a proximal end 292 and a distal end 294. The proximal end 292 is located at the first axial end 152 of the fixed handle 150 and the distal end 294 is located at the clamp 280. A lumen 296 (FIG. 16) extends axially through the reduction device 12 from the proximal end 292 to the distal end 294. The bore 268 in the carriage 244 of the translating mechanism 240, the bore 178 in the fixed handle 150, and the passage 290 formed by the actuator shaft 106 and fixed shaft 16 define the lumen 296. The threaded surface 270 defining the bore 268 in the carriage 244 forms a threaded portion of the lumen 296.

The drive device 14 (FIG. 1) includes a driver 300 and a driver spring 302. The driver extends axially along axis A and includes first and second axial end portions 304 and 306, respectively, and an intermediate portion 308. The intermediate portion 308 of the driver 300 is a cylindrical shaft.

The first axial end portion 304 of the driver 300 includes a tool receiving portion 310 and a drive portion 312. A cylindrical shaft 314 interconnects the tool receiving portion 310 and the drive portion 312. The tool receiving portion 310 of the driver 300 is hexagonal and includes an annular recess 316 for locking a drive tool (not shown) to the driver 300. An end surface 318 (FIG. 16) of the tool receiving portion 310 forms a first axial end of the driver 300. The drive portion 312 of the first axial end portion 304 of the driver 300 is cylindrical and has a larger diameter than the remainder of the driver 300. The outer surface 320 of the drive portion 312 is threaded.

The second axial end portion 306 of the driver 300 includes a centering portion 322 and a drive portion 324. A cylindrical shaft 326 interconnects the centering portion 322 and the drive portion 324. The centering portion 322 of the driver 300 is cylindrical and has a diameter that is larger than the shaft 326 and is smaller than the drive portion 312 of the first axial end portion 304 of the driver 300. The drive portion 324 of the second axial end portion 306 of the driver 300 is hexagonal. An end surface 328 (FIG. 12) of the drive portion 324 forms a second axial end of the driver 300.

As shown in FIG. 12, a cylindrical bore 330 extends into the end surface 328 at the second axial end of the driver 300. The bore 330 extends axially through the drive portion 324 and partially into the shaft 326 of the second axial end portion 306 of the driver 300. A window 332 extends radially through the shaft 326 of the second axial end portion 306 of the driver 300 and connects to the bore 330.

As shown in FIG. 12, the driver spring 302 includes a stepped shaft 340 and a head portion 342. The stepped shaft 340 includes first and second tubular portions 344 and 346, respectively. The first tubular portion 344 forms a first axial end of the driver spring 302 and connects to the second tubular portion 346. The second tubular portion 346 has an outer diameter that is slightly larger than an outer diameter of the first tubular portion 344. The inner diameters of the first and second tubular portions are the same and collectively form a passage 348 through the stepped shaft 340.

The head portion 342 of the driver spring 302 is connected to the second tubular portion 346 of the stepped shaft 340, opposite the first tubular portion 344. As shown in FIG. 13, the head portion 342 of the driver spring 302 is generally square and includes four side surfaces 350 and an end surface 352. Corners 354, connecting adjacent side surfaces 350, are rounded. The side surfaces 350 and the corners 354 taper radially inwardly toward the end surface 352. The taper of the corners 354 is greater than the taper of the side surfaces 350 so that the end surface 352 is generally circular.

An opening 356 extends through the center of the head portion 342 and connects to the passage 348 of the stepped shaft 340. The diameter of the opening 356 is the same as the inner diameters of the first and second tubular portions 344 and 346 of the stepped shaft 340.

Four grooves 358 extend axially through the head portion 342 and through a portion of the second tubular portion 346 of the driver spring 302. FIG. 12 shows one groove 358 extending axially through a portion of the second tubular portion 346 of the driver spring 302. In the head portion 342 of the driver spring 302, the four grooves 358 extend radially between the opening 356 and the side surfaces 350, as shown in FIG. 13. In the second tubular portion 346 of the driver spring 302, the four grooves 358 extend between the inner diameter and the outer diameter. Each side surface 350 of the head portion 342 has an associated groove 358. The associated groove 358 extends through the center of the side surface 350. The four grooves 358 enable the head portion 342 of the driver spring 302 to be compressed radially inwardly when subjected to a radially inwardly directed force. The head portion 342 resiliently returns to its original shape when the radially inwardly directed force is removed.

To assemble the drive device 14, the first tubular portion 344 of the driver spring 302 is inserted into the bore 330 on the second axial end of the driver 300. When the head portion 342 of the driver spring 302 is near the second axial end of the driver 300, the first tubular portion 344 of the driver spring 302 is fixed to the driver 300. Preferably, the first tubular portion 344 of the driver spring 302 is either soldered to or welded to the driver 300 with access to the first tubular portion 344 being provided through the window 332.

The surgical instrument 10 of the present invention may be used for moving a vertebra relative to another vertebra, preferably along the sagittal plane of a body 360 during a surgical procedure. The surgical procedure may include open surgery. Preferably, the surgical procedure is performed through a cannula 368.

Figure 19:
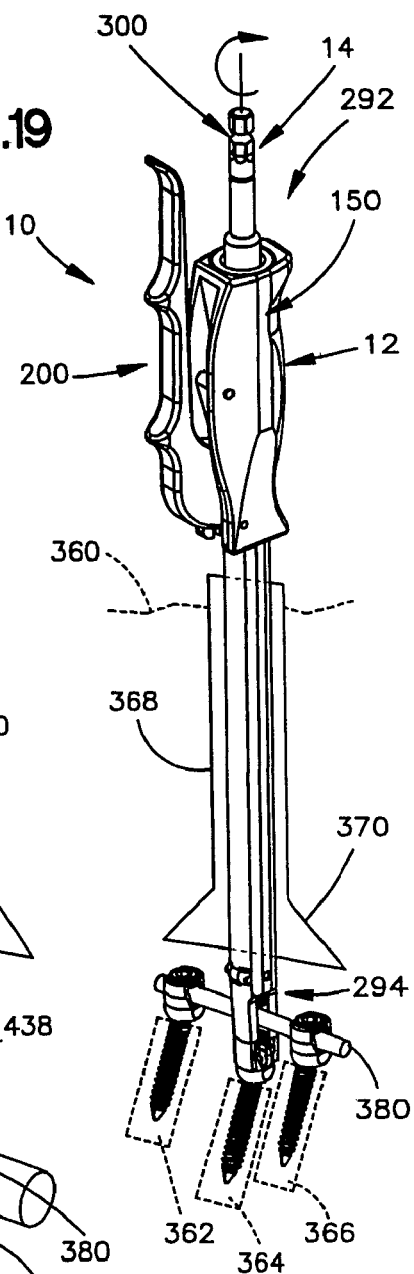
FIG. 19 illustrates the surgical instrument of FIG. 1 being used to move a vertebra.

FIG. 19 illustrates three vertebrae 362, 364, and 366. Vertebra 364 is moved or slipped along the sagittal plane of the body 360 relative to vertebrae 362 and 364. FIG. 19 also illustrates the cannula 368 having an expandable distal end or skirt portion 370. An exemplary cannula is disclosed in U.S. Pat. No. 6,187,000 B1, which is incorporated herein by reference in its entirety. As set forth therein, the cannula can be configured in size to permit the simultaneous use of a number of endoscopic surgical instruments, including, but not limited to, steerable instruments, shavers, dissectors, scissors, forceps, retractors, dilators, and video cameras. The cannula 368 provides a passage into the body 360. The expanded skirt portion 370 of the cannula 368 defines an operative space that provides access to all three vertebrae 362, 364, and 366. An endoscope (not shown) may be extended through the cannula 368 for providing vision within the operative space.

Figure 20:
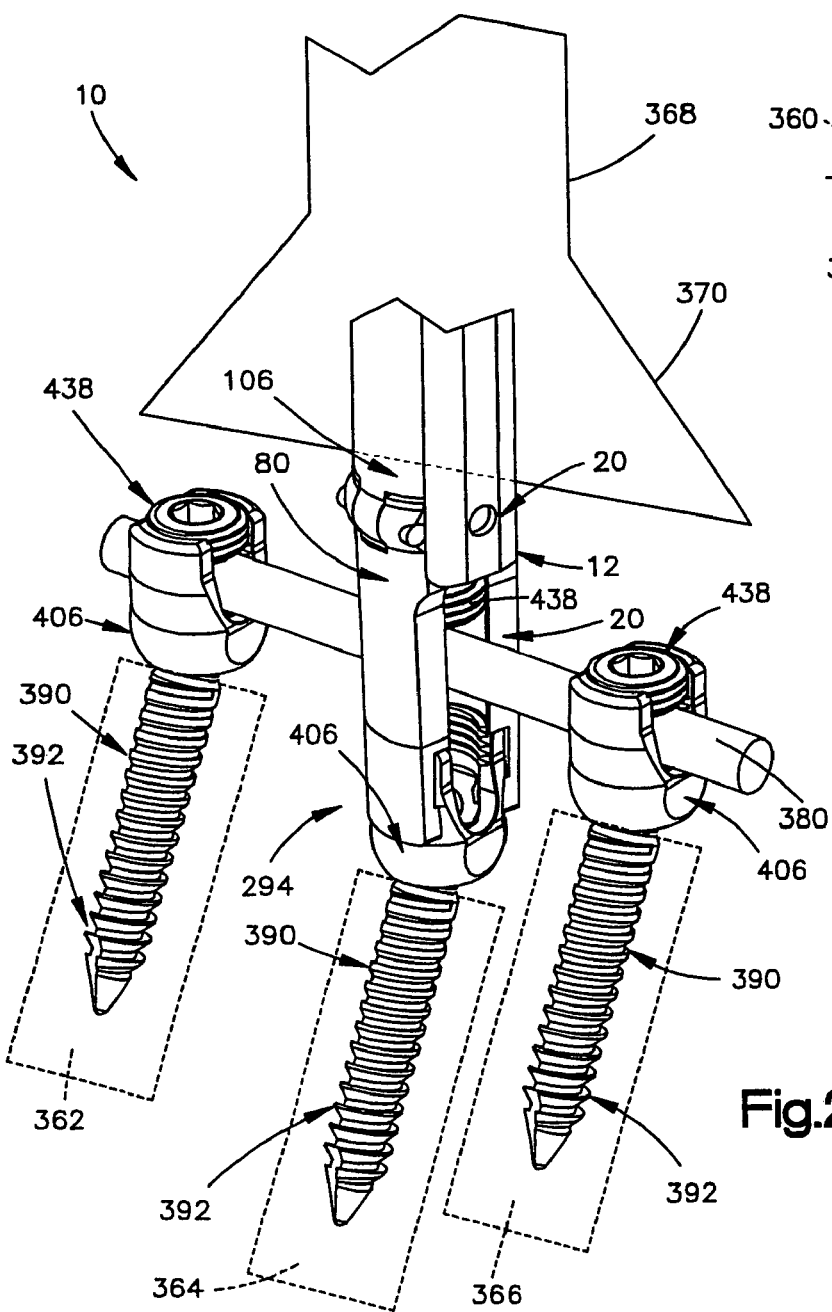
FIG. 20 is an enlarged portion of FIG. 19.

FIG. 20 illustrates a surgically implantable longitudinal member or rod 380 for maintaining bone portions, such as vertebrae of a spinal column, in a desired spatial relationship. The rod 380 is made of a suitable biocompatible material. The rod 380 illustrated in FIG. 20 has a length that is sufficient to span the three vertebrae 362, 364, and 366. The length of the rod 380 in any particular installation will depend upon the condition to be corrected and the number of vertebrae to be held in a desired spatial relationship relative to each other by the rod 380.

Fasteners 390 connect the rod 380 with vertebrae of the spinal column. Each fastener 390 is made of a suitable biocompatible material. Each fastener 390 illustrated in FIG. 20 is identical. Therefore, only one of the fasteners 390 is described in detail.

Figure 17:
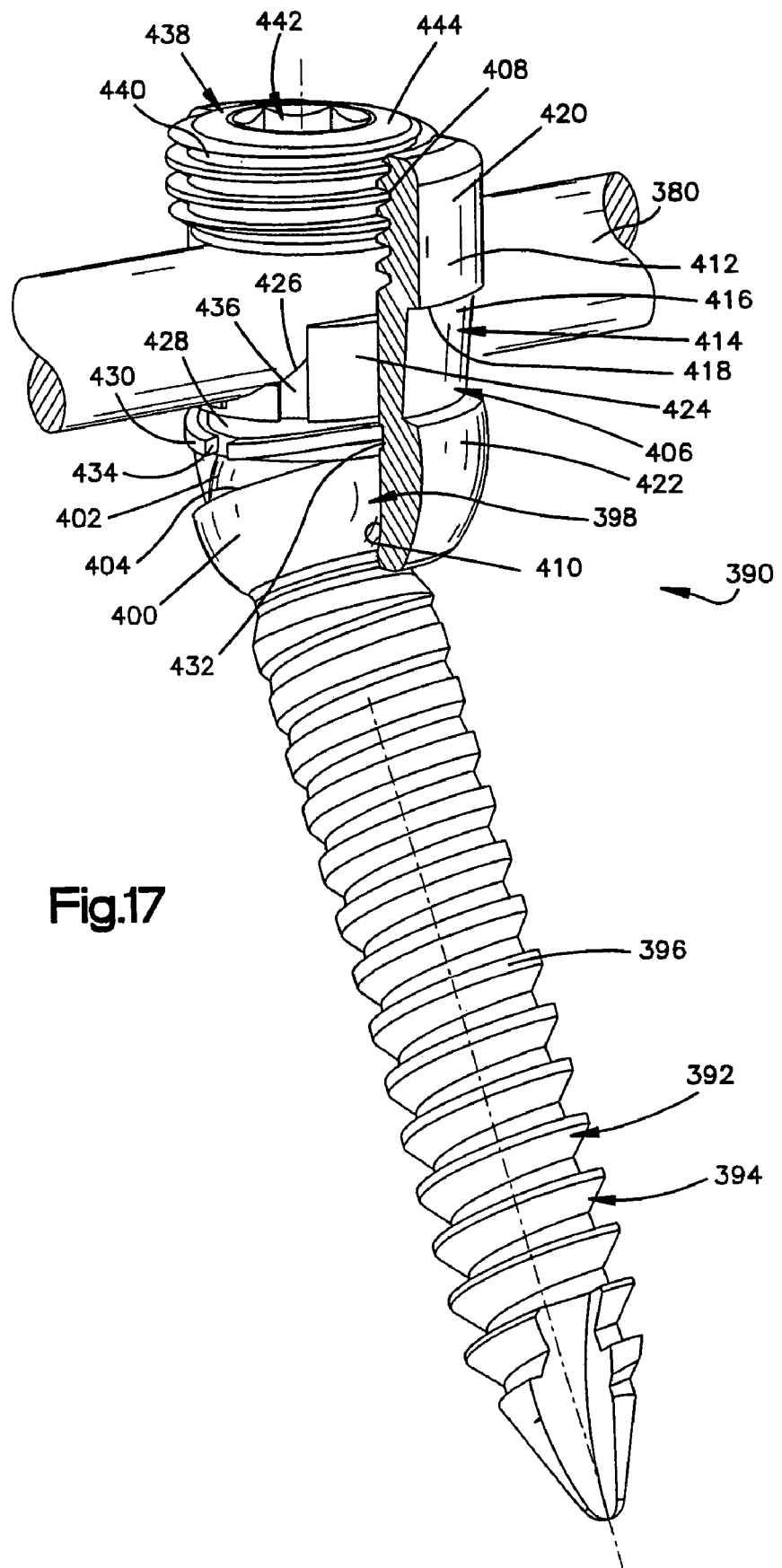
FIG. 17 is a perspective view, partially in section, of a fastener for use with the surgical instrument of FIG. 1.

With reference to FIG. 17, the fastener 390 includes a shank 392. The shank 392 has a threaded portion 394 having a course thread convolution 396 for engaging the vertebra. A head portion 398 of the shank 392 is provided with first and second spherical surfaces 400 and 402, respectively. The second spherical surface 402 has a diameter less than a diameter of the first spherical surface 400. A radially extending shoulder 404 extends between the first and second spherical surfaces 400 and 402. A recess (not shown) is provided in the second spherical surface 402 of the head portion 398 of the shank 392 for receiving a tool (not shown) that applies torque to the shank 392 to turn the thread convolution 396 into a vertebra.

The shank 392 extends into a housing 406 of the fastener 390 that interconnects the rod 380 and the shank 392. The housing 406 has a laterally extending passage through which the rod 380 extends and a longitudinal passage that extends transverse to the lateral passage and intersects the lateral passage within the housing 406. The longitudinal passage includes a top opening defined by a threaded inner surface 408 and a lower opening that is defined by a concave inner surface 410. The shank 392 is inserted through the top opening in the housing 406 and the threaded portion 394 of the shank 392 extends outwardly of the housing 406 through the lower opening. The first spherical surface 400 of the shank 392 engages a concave spherical surface 410 of the housing 406 adjacent the narrow opening. Accordingly, the shank 392 is pivotal relative to the housing 406 into a plurality of angular positions.

An outer surface 412 of the housing 406 includes a circumferentially extending groove 414 that includes a smooth bottom surface 416. A radially outwardly extending shoulder 418 defines an upper side wall of the groove 414 and connects to an upper rim surface 420. An arced lower rim surface 422 defines a lower side wall of the groove 414.

A spacer 424 is received in the longitudinal passage of the housing 406. The spacer 424 has a concave spherical bottom surface (not shown) that engages the second spherical surface 402 of the shank 392. The shoulder 404 on the shank 392 engages the spacer 424 to limit the relative movement between the shank 392 and the housing 406. The spacer 424 also has a concave cylindrical upper surface 426 that engages the rod 380. An opening (not shown) extends through the spacer 424 to receive the tool (not shown) that engages the recess in the shank 392.

The spacer 424 has a circumferential groove 428 for receiving a compressible member such as a spring member 430. An inner surface of the housing 406 includes a circumferential groove 432 for receiving the spring member 430 so that the spring member 430 extends from the groove 428 in the spacer 424 to the groove 432 in the housing 406. The spring member 430 is a ring having a gap 434 that permits radial contraction and expansion of the spring member 430.

The spring member 430 urges the spacer 424 axially toward the shank 392 to press the housing 406 against the first spherical surface 400 of the shank 392. The spherical bottom surface of the spacer 424 frictionally engages the second spherical surface 402 of the shank 392 and the first spherical surface 400 of the shank 392 frictionally engages the housing 406. The shank 392 and the housing 406 are manually movable relative to each other by a surgeon when the rod 380 is disengaged from the spacer 324.

The spacer 324 has four axially extending slots 436, one of which is shown in FIG. 17. The slots 436 intersect the groove 428. A tool (not shown) having four prongs may be extended through the slots 436 and into engagement with the spring member 430. The tool grasps the spacer 424 and the spring member 430 for inserting the spacer 424 and the spring member 430 into the housing 406. The prongs of the tool engage the spring member 430 to radially contract the spring member 430 into the groove 428 in the spacer 424. The prongs hold the spring member 430 in the radially contracted condition in the groove 428 while the spacer 424 and spring member 430 are inserted into the housing 406. Once the spacer 424 engages the shank 392, the prongs are removed from the slots 436 and the spring member 430 radially expands into the groove 432 in the housing 406. Although the spacer 424 is described as having four slots 436, the spacer 424 could have any number of slots 436 and the tool would have the same number of prongs as the spacer 424 has slots 436.

A threaded member or setscrew 438 having a threaded outer surface 440 is received in the threaded top opening of the housing 406. When screwed into the housing 406, the setscrew 438 engages the rod 380 and applies a force to the rod 380 to press the rod against the spacer 424 and the spacer against the shank 392. The setscrew 438 clamps the rod 380, the spacer 424, and the housing 406 to the shank 392 to prevent movement of the shank 392 relative to the housing 406. After the setscrew 438 secures the rod 380 relative to the housing 406, the shank 392 is no longer movable relative to the housing 406. Thus, the setscrew 438 locks the shank 392 and the housing 406 relative to one another.

Figure 18:
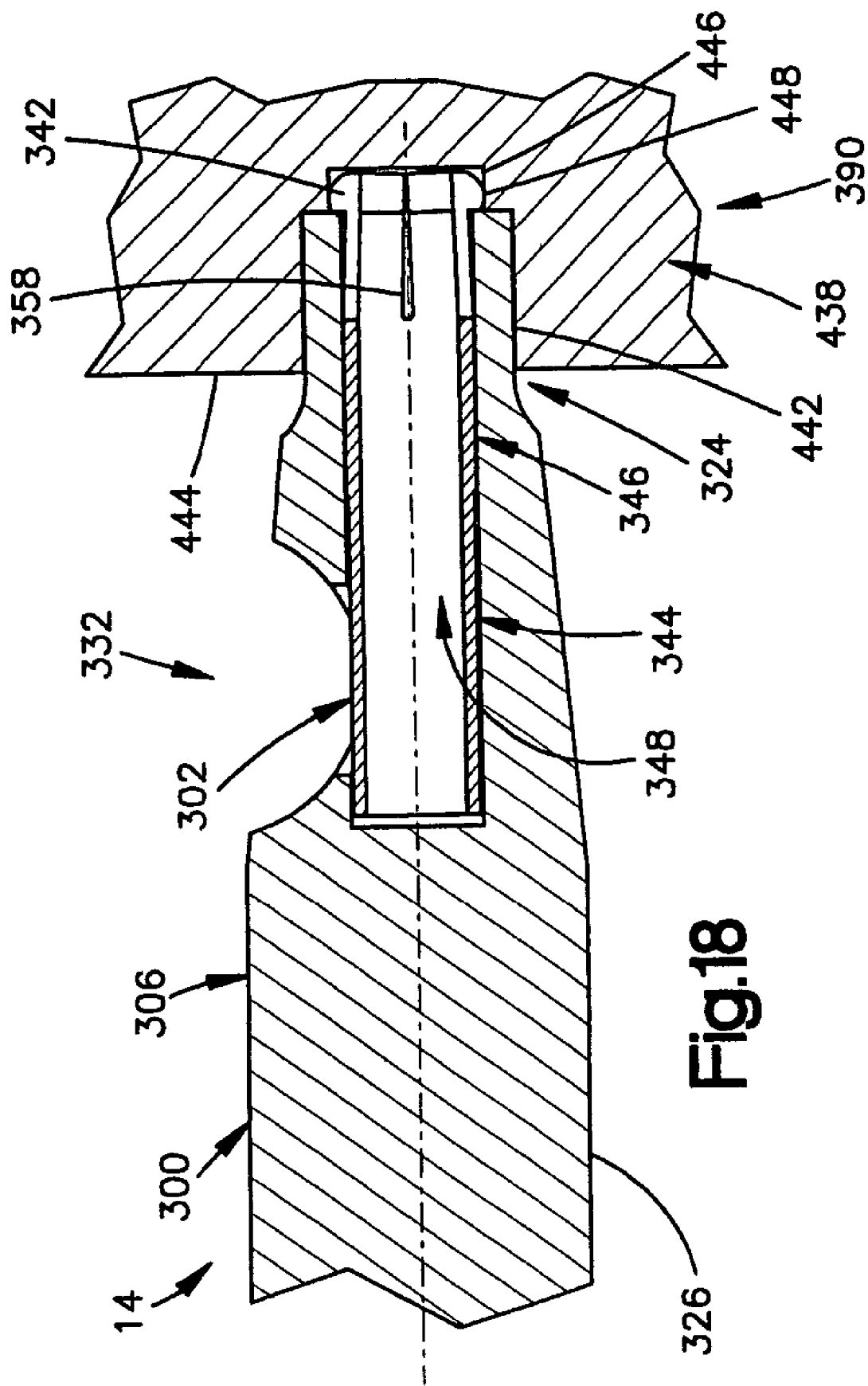
FIG. 18 illustrates a setscrew of the fastener of FIG. 17 held on the second axial end of the drive device of the surgical instrument of FIG. 1.

FIG. 18 shows a partial cross-section of the setscrew 438 of the fastener 390. A hexagonal bore 442 extends into an upper surface 444 of the setscrew 438. The hexagonal bore 442 is sized to receive the drive portion 324 of the second axial end portion 306 of the driver 300. A cylindrical bore 446, which is defined by cylindrical surface 448, extends into the setscrew 438 below the hexagonal bore 442. The cylindrical bore 446 and the hexagonal bore 442 are coaxial. A diameter of the cylindrical bore 446 is less than a width across the hexagonal bore 442 and is also less than the distance between rounded corners 354 of the head portion 342 of the driver spring 302.

The driver spring 302 holds the setscrew 438 on the drive device 14. The hexagonal drive portion 324 of the driver 300 is adapted to fit in the hexagonal bore 442 of the setscrew 438. When the drive portion 324 of the driver 300 is received in the hexagonal bore 442 of the setscrew 438, the driver spring 402 is received in the cylindrical bore 446 of the setscrew 438 for holding the setscrew on the drive device 14.

FIG. 18 illustrates the driver spring 302 holding the setscrew 438 on the drive device 14. When inserted into the cylindrical bore 446 of the setscrew 438, the side surfaces 350 of the driver spring 302 are forced together. The grooves 358 of the driver spring 302 enable the side surfaces 350 to move toward one another during axial movement of the driver spring 302 into the cylindrical bore 446. The four rounded corners 354 of the driver spring 302 press radially outwardly into contact with the cylindrical surface 448 defining the cylindrical bore 446 to hold the setscrew 438 on the drive device 14. To remove the setscrew 438 from the driver spring 302, the setscrew 438 is pulled axially off of the driver spring 302. The force of the driver spring 302 holding the setscrew 438 is sufficient to enable the setscrew 438 to be held vertically below the drive device 14.

As shown in FIG. 19, fasteners 390 are secured in each of the vertebrae 362, 364, and 366. The rod 380 extends between vertebrae 362 and 366 and is locked in place relative to vertebrae 362 and 366. As shown in FIG. 20, the housing 406 attached to the shank 392 of the fastener 390 secured in vertebra 364 is spaced, along the sagittal plane of the body 360, from the rod 380. The surgical instrument 10 of the present invention moves vertebra 364 along the sagittal plane 20 of the body 360 and relative to vertebrae 362 and 366 so that the fastener 390 attached to vertebra 364 may be fastened to the rod 380.

To move vertebra 364 along the sagittal plane of the body 360, the distal end 294 of the reduction device 12 is inserted into the body 360 through the passage of the cannula 368. When the distal end 294 of the reduction device 12 is located in the operative space, the actuator handle 200 is pivoted away from the fixed handle 150 to move the actuator shaft 106 toward the proximal end 292 of the reduction device 12 and pivot the pivotal jaw 80 into an open position opening the clamp 280. The distal end 294 of the reduction device 12 is moved within the operative space to a position in which the rod 380 is located adjacent the inner surface 64 of the linking portion 58 of the fixed jaw 20 and the gripping portion 62 of the fixed jaw 20 is positioned in the circumferential groove 414 of the housing 406 attached to vertebra 364. When the gripping portion 62 of the fixed jaw 20 is positioned in the circumferential groove 414, the upper rim surface 420 of the housing 406 is received in the mouth portion 60 of the fixed jaw 20.

The actuator handle 200 is then pivoted toward the fixed handle 150 of the reduction device 12. As a result, the actuator shaft 106 is moved toward the distal end 294 of the reduction device 12 and the pivotal jaw 80 is closed or pivoted toward the fixed jaw 20 to close the clamp 280. During closure of the clamp 280, the distal end 294 of the reduction device 12 is manipulated so that the gripping portion 90 of the pivotal jaw 80 is positioned in the circumferential groove 414 of the housing 406 opposite to the gripping portion 62 of the fixed jaw 20 and the upper rim surface 420 of the housing 406 is received in the mouth portion 88 of the pivotal jaw 80 opposite the mouth portion 60 of the fixed jaw 20. Thus, when the actuator handle 200 is pivoted toward the fixed handle 150, the housing 406 attached to vertebra 364 becomes locked in the clamp 280 formed between the fixed and pivotal jaws 20 and 80 of the reduction device 12 with the rod 380 located between the linking portions 58 and 86 of the fixed and pivotal jaws 20 and 80, respectively.

The second axial end of the drive device 14, with a setscrew 438 attached to the driver spring 302, is then inserted into the lumen 296 of the reduction device 12 and is moved toward the distal end 294 of the reduction device until the threaded drive portion 312 of the driver 300 engages the threaded inner surface 270 of the carriage 244. A tool (not shown), such as a T-handle ratchet, attached to the tool receiving portion 310 of the driver 300 is manipulated to rotate the drive device 14. During rotation of the drive device 14, the, threaded drive portion 312 of the driver 300 engages the threaded inner surface 270 of the carriage 244 and results in the drive device 14 moving axially along the lumen 296 and relative to the carriage 244 of the reduction device 12.

Figure 24:
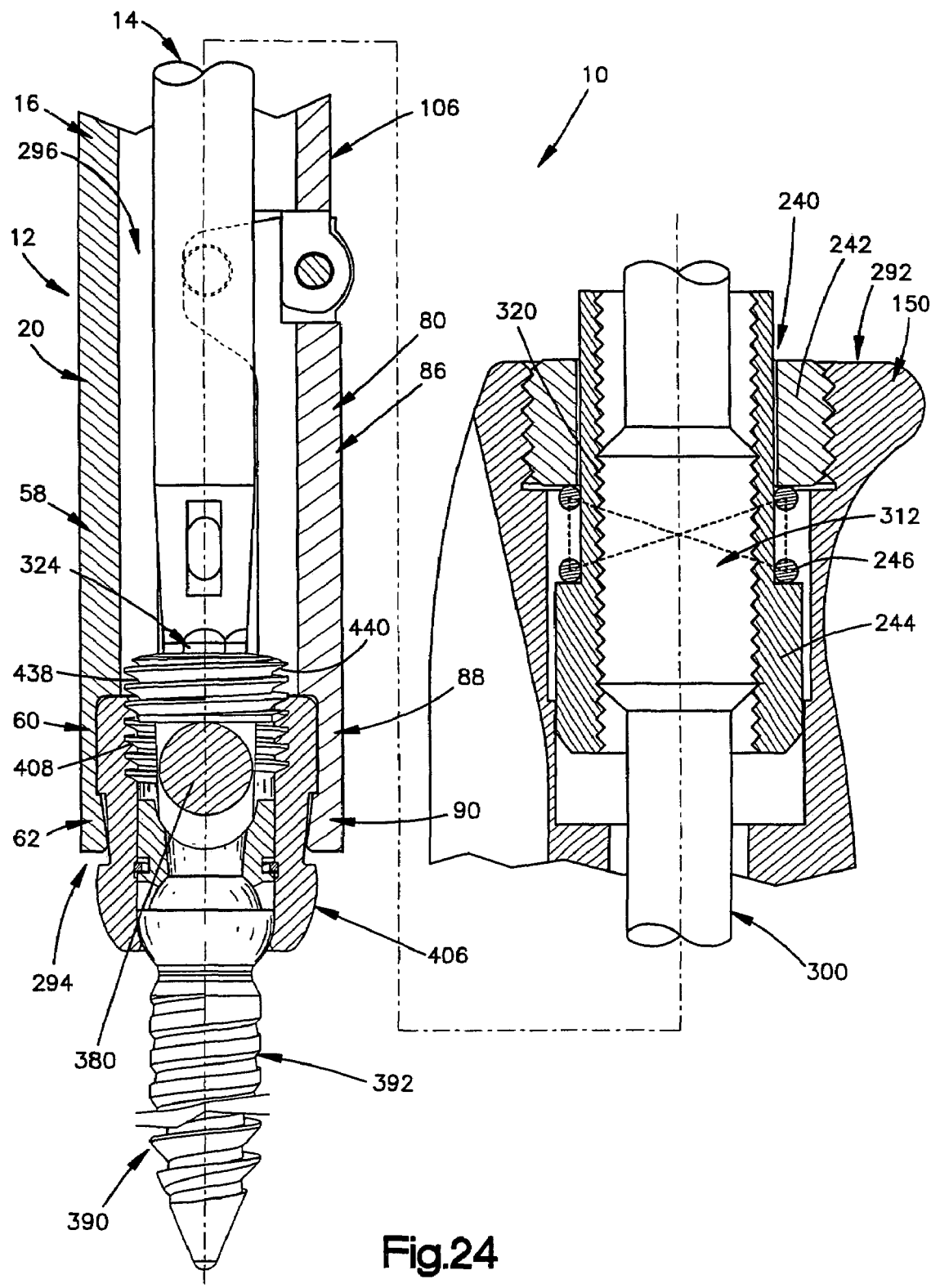
FIG. 24 is a cross-sectional view of a portion of the surgical instrument of FIG. 1 inserting a setscrew into the fastener of FIG. 17 to secure a vertebra to a rod.

The drive device 14, which is holding on the setscrew 438, presses the setscrew 438 against the rod 380. Rotation of the drive device 14 relative to the reduction device 12 and within the carriage 244 results in an axially directed drive force that tends to move the fastener 390 in vertebra 364 toward rod 380. When the force necessary to move vertebra 364 relative to vertebrae 362 and 366 is less than the axially directed drive force and is less than the predetermined axial load of the spring 246 on the carriage 244, relative rotation between the reduction device 12 and the drive device 14 moves vertebra 364 relative to vertebrae 362 and 366. Thus, when the drive force is less than the spring force, the clamp 280 of the reduction device 12, which is clamped to the fastener 390 fixed to vertebra 364, is moved relative to the drive device 14 during rotation of the drive device relative to the reduction device 12 so that the fastener 390 fixed to vertebra 364 is moved closer to the rod 380. During this movement, the part or carriage 244 is stationary relative to the fixed handle 150. Continued rotation of the drive device 14 relative to the reduction device 12, moves vertebra 364 relative to vertebrae 362 and 366 and into a position in which the rod 380 is partially received in the housing 406 of the fastener 390 fixed to vertebra 364 and the threaded surface 408 of the housing 406 is brought into contact with the threaded outer surface 440 of the setscrew 438, as shown in FIG. 24.

When the drive force is greater than the predetermined axial load of spring 246 on the part or carriage 244, rotation of the drive device 14 relative to the reduction device 12 moves the carriage 244 of the translating mechanism 240 toward the cap 242 causing the spring 246 to be compressed. Since the interaction between the planar surfaces 266 of the head portion 258 of the carriage 244 and the planar surfaces 196 and 198 defining the non-cylindrical bore 186 prevent the carriage 244 from rotating relative to the fixed handle 150 of the reduction device 12, rotation of the drive device 14 relative to the reduction device 12 results in only translation or axial movement of the carriage 244 relative to the fixed handle 150. Thus, when the drive force is greater than the spring force, the translation of the part or carriage 244 results in rotation of the drive device 14, and thus the setscrew 438, relative to the reduction device 12 without any relative axial movement between the drive device 14 and the clamp 280 of the reduction device 12. As the spring 246 of the translation device 240 is compressed, the spring force or predetermined axial load increases. When the spring force becomes greater than the drive force, the drive force again acts to move the drive device 14 axially relative to the clamp 280 of the reduction device 12.

When the threaded outer surface 440 of the setscrew 438 contacts the threaded inner surface 408 of the housing 406 of the fastener 390 fixed to vertebra 364, an interaction between the threads of the threaded surfaces 408 and 440 may resist further relative axial movement between vertebra 364 and vertebrae 362 and 366. As a result, the drive force necessary to continue axial movement of vertebra 364 relative to vertebrae 362 and 366 increases. If the drive force remains below the spring force, relative rotation between the drive device 14 and the reduction device 12 results in rotation of the setscrew 438 relative to the housing 406 and moves the setscrew 438 axially into the housing 406 to lock vertebra 364 relative to the rod 380.

Misalignment of the threaded outer surface 440 of the setscrew 438 and the threaded inner surface 408 of the housing 406 may result in the drive force increasing above the spring force. When the drive force becomes greater than the spring force, further rotation of the drive device 14 relative to the reduction device 12 results in axial movement of the carriage 244 away from vertebra 364 and toward cap 242. As a result of the axial movement of the carriage 244, relative rotation between the drive device 14 and the reduction device 12 results in the setscrew 438 rotating relative to the housing 406 of the fastener 390 fixed to vertebra 364 but does not cause any translation or relative axial movement between the setscrew 438 and the housing 406. Rotation of the setscrew 438 without translation of the setscrew relative to the housing 406 enables proper alignment of the threaded surfaces 440 and 408 of the setscrew 438 and the housing 406 before the setscrew is screwed or threaded into the housing. As a result, cross-threading between the setscrew 438 and the housing 406 is prevented. When the threaded surfaces 440 and 408 of the setscrew 438 and the housing 406 are properly aligned, rotation of the drive device 14 screws or threads the setscrew 438 into the housing 406 to secure vertebra 364 to the rod 380.

Figure 25:
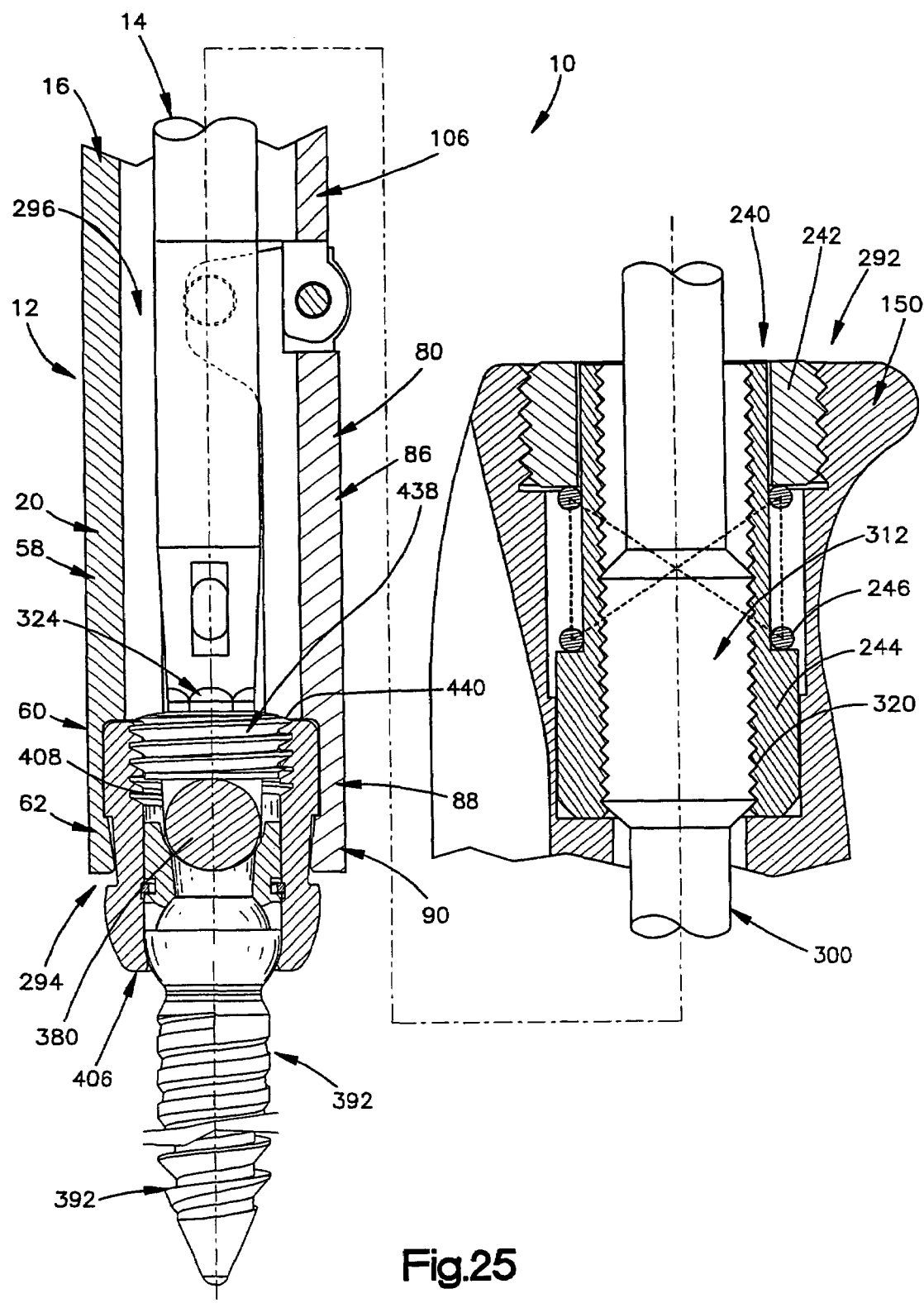
FIG. 25 is a cross-sectional view of a portion of the surgical instrument of FIG. 1 after complete insertion of the setscrew into the fastener of FIG. 17 to secure a vertebra to a rod.

When the setscrew 438 is secured in the housing 406 and vertebra 364 is secured to the rod 380, as is shown in FIG. 25, the drive device 14 is pulled upwardly and out of the proximal end 292 of the reduction device 12. The actuator handle 200 of the reduction device 12 is then moved away from the fixed handle 150 to pivot the pivotal jaw 80 and open the clamp 280. The reduction device 12 may then be removed from the housing 406 of the fastener 390, and removed from the cannula 368. Then, the cannula 368 may be removed from the body 360 and the body may be sutured in an appropriate manner.

Figure 26:
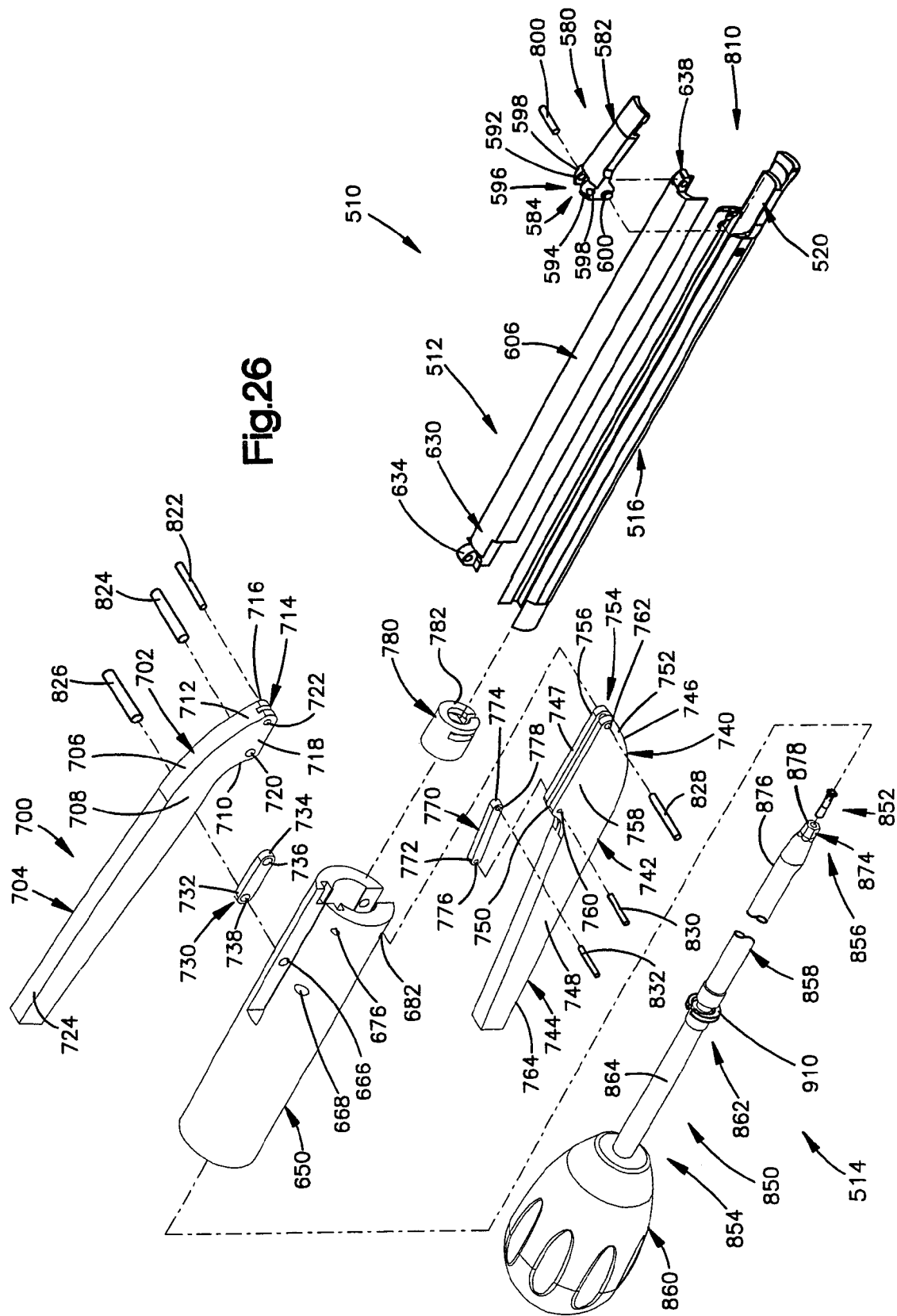
FIG. 26 is an exploded, perspective view of a surgical instrument constructed in accordance with a second embodiment.

FIG. 26 is an exploded perspective view of a surgical instrument 510 constructed in accordance with a second embodiment. The surgical instrument 510 includes a reduction device 512 and a drive device 514.

The reduction device 512 includes a fixed shaft 516 that is formed from a biocompatible material. As shown in FIGS. 27-28, the fixed shaft 516 includes a main body portion 518 and a fixed jaw 520. The main body portion 518 extends axially between first and second axial ends 522 and 524. The main body portion 518 has a generally C-shaped cross-section, as shown in FIGS. 29-31. A bottom wall 526 and opposite first and second side walls 528 and 530 define the C-shaped cross-section of the main body portion 518 of the fixed shaft 516 The bottom wall 526 is arced and includes arcuate inner and outer surfaces 532 and 534. The inner surface 5;2 of the bottom wall 526 is centered at point 536. The bottom wall 526 terminates at first and second end surfaces 538 and 540. An arc length of the bottom wall of the fixed shaft is less than 180 degrees about point 536.

The first and second side walls 528 and 530 of the main body portion 538 of the fixed shaft 516 extend upwardly from the first and second end surfaces 538 and 540. The first and second side walls 528 and 530 include planar inner and outer surfaces 542 and 544 that are connected by curved end surfaces 546. The inner surface 542 of the first side wall 528 extends upwardly from a lateral midpoint of the first end surface 538 of the bottom wall 526 in a direction perpendicular to the first end surface 538. The outer surface 544 of the first side wall 528 extends parallel to the inner surface 542 and is contiguous with the outer surface 534 of the bottom wall 526. The inner surface 542 of the second side wall 530 extends upwardly from a lateral midpoint of the second end surface 540 of the bottom wall 526 in a direction perpendicular to the second end surface 540 of the bottom wall 526. The outer surface 544 of the second side wall 530 extends parallel to the inner surface 542 and is contiguous with the outer surface 534 of the bottom wall 526.

The arcuate inner surface 532 of the bottom wall 526 and the parallel inner surfaces 542 of the first and second side walls 528 and 530 collectively define a channel 548 (FIG. 29) in the main body portion 518 of the fixed shaft 516. An open top of the fixed shaft 516 leads into the channel 548.

First and second, coaxial through-holes 550 and 552, respectively, extend through the first and second side walls 528 and 530, respectively, adjacent the second axial end 524 of the main body portion 518 of the fixed shaft 516. The centers of the first and second through-holes 550 and 552 are aligned with point 536.

A slot 554 extends into the inner surface 542 of the first side wall 528 of the main body portion 518 of the fixed shaft 516 adjacent the first end surface 538 of the bottom wall '26. As shown in FIG. 28, the slot 554 in the first side wall 528 extends from the first axial end 522 of the main body portion 518 and terminates adjacent the first through-hole 550 near the second axial end 52A of the main body portion 518. The slot 554 is open on the first axial end 522 and is closed on the second axial end 524. The slot 554 partially intersects a lower portion of the first through-hole 550.

A slot 556 extends into the inner surface 542 of the second side wall 530 of the main body portion 518 adjacent the second end surface 540 of the bottom wall 526. As shown in FIG. 27, the slot 556 in the second side wall 530 extends from the first axial end 522 of the main body portion 518 and terminates adjacent the second through-hole 552 near the second axial end 524 of the main body portion 518. The slot 556 is open on the first axial end 522 and is closed on the second axial end 524. The slot 556 partially intersects a lower portion of the second through-hole 552.

The fixed jaw 520 of the fixed shaft 516 extends axially outwardly of the bottom wall 526 of the main body portion 518 of the fixed shaft 516. The fixed jaw 520 includes a linking portion 558, a mouth portion 560 and a gripping portion 562.

As shown in FIGS. 27-28, an inner surface 564 of the linking portion 558 is arcuate and is formed by an axial extension of the inner surface 532 of the bottom wall 526. The mouth portion 560 of the fixed jaw 520 includes an arcuate inner surface 566. A shoulder 568 connects the inner surface 566 of the mouth portion 560 to the inner surface: 564 of the linking portion 558. The gripping portion 562 includes a tapered inner surface 570. A shoulder 572 connects the inner surface 566 of the youth portion 560 to the tapered inner surface 570 of the gripping portion 562. The tapered inner surface 570 of the gripping portion 562 widens near a terminal end 574 (FIG. 28) of the fixed jaw 520. An outer surface 576 of the fixed jaw 520 is arcuate. The inner surface 566 of the mouth portion 560 is recessed, or nearer the outer surface 576 of the fixed jaw 520, relative to the inner surfaces 564 and 571 of the linking portion 558 and the gripping portion 562.

The reduction Device 512 also includes a pivotal jaw 580 (FIG. 26). The pivotal jaw 580 includes a main body portion 582 and a pivotal portion 584. The main body portion 582 of the pivotal jaw 580 is a mirror image of the fixed law 520 of the fixed shaft 516. The pivotal jaw 580 also includes a linking portion 586, a mouth portion 588, and a gripping portion 590.

As shown in FIG. 26, the pivotal portion 584 of the pivotal jaw 580 includes first and second members 592 and 594 respectively, that are separated from one another by a central channel 596. Laterally extending through-holes 598 extend through an upper portion of the first and second members 592 and 594. A cylindrical pivot element 600 extends laterally outwardly of a lower portion of each of the first and second members 592 and 594.

The reduction device 512 also includes an actuator shaft 606, shown in detail in FIGS. 31-32. The actuator shaft 606 extends axially between first and second axial ends 638 and 610, respectively. An arcuate upper wall 512 and parallel side walls 614 and 616 define a generally C-shaped cross-section of the actuator shaft 606. The arcuate upper wall 612 includes inner and outer surfaces 618 and 620, respectively. The outer surface 620 of the upper wall 612 has a larger radius of curvature than the inner surface 618. The inner surface 618 is centered on point 622.

The side walls 614 and 616 of the actuator shaft 606 extend downwardly from the upper wall 612 beyond point 622. Each side wall 614 and 616 includes parallel inner and outer surfaces 624 and 626, and terminates at a lower end surface 628. The actuator shaft 606 has a width, measured laterally between the outer surfaces 626 of the side walls 614 and 616, that is sized to fit within the channel 548 of the fixed shaft 516 so that each side wall 614 and 616 of the actuator shaft 606 extends adjacent to an associated side wall 528 and 530 of the fixed shaft 516.

A first linking element 630 of the actuator shaft 606 extends axially outwardly of the first axial end 608 of the actuator shaft 606. The first linking element 630 includes an axial extension 632 and a linking member 634. The axial extension 632 extends axially outwardly of the first axial end 608 of the actuator shaft 606 and supports the linking member 634.

The linking member 634 extends axially outwardly of the axial extension 632. A laterally extending through-hole 636 extends through the linking member 634.

A second linking element 638 extends axially outwardly of the second axial end 610 of the actuator shaft 606. A laterally extending through-hole 640 extends through the second linking element 638.

FIGS. 33-35 illustrate a fixed handle 650 of the reduction device 512. An axial length of the fixed handle 650 is defined between first and second axial ends 652 and 654. The fixed handle 650 is cylindrical and includes an axially extending channel 664 (FIG. 34), which is open at the top. A width of the channel 664 is defined between upper portions 660 and 662 of the fixed handle 650.

First and second through-holes 666 and 668, (FIG. 26) extend though the upper portions 660 and 662 to connect to the channel 664. The first and second through-holes 666 and 668 are coaxial with one another.

First and second axially extending slots 670 and 672 (FIG. 35), each of which is open to channel 664, extend into the upper portions 660 and 662 adjacent the second axial end 654 of the fixed handle 650. Each of the first and second slots 670 and 672 is located radially inwardly, relative to axis A, from the first and second through-holes 666 and 668. The first slot 670 extends axially along the upper portion 660. A through-hole 674 extends through the upper portion 6:0 and intersects the first slot 670. A through-hole 676 extends through the upper portion 662 and intersects the second slot 672.

The fixed handle 650 includes an axially extending channel 678, which is open at the bottom. A width of the channel 678 is defined between lower portions 656 and 658 of the fixed handle 650. Through-holes 680 and 682 (FIGS. 26-33) extend through the lower portions 656 and 658 to connect to the channel 678. The through-holes 680 and 682 are coaxial with one another.

A bore 684 extends axially through the fixed handle 650 from the first axial end 652 to the second axial end 654. The bore 684 (FIG. 34) is cylindrical. It is contemplated that the bore 684 may have any desired shape.

An actuation handle 700 (FIG. 26) of the reduction device 512 includes a main body portion 702 and an axially extending actuator portion 704. The main body portion 702 of the actuator handle 700 includes a rounded upper surface 706, a bottom surface (not shown), and planar first and second side surfaces 708. Only the second side surface 708 is shown in FIG. 26. The main body portion 702 of the actuator handle 700 also includes first and second axial ends 710 and 712.

An axially extending channel 714 extends into the bottom surface of tie actuator handle 700 to define first and second flanges 716 and 718. The first flange 716 extends between the first and second axial ends 710 and 712 of the main body portion 702 adjacent the first side surface. The second flange 718 extends between the first aid second axial ends 710 and 712 of the main body portion 702 adjacent the second side surface 708. Coaxial through-holes 720 (only one of which is shown) extend through the first and second flanges 716 and 718 adjacent the first axial end 710 of the main body portion 702. Coaxial through-holes 722 (only one of which is shown) extend through the first and second flanges 16 and 718 adjacent the second axial end 712 of the main body portion 702.

The actuator portion 704 of the actuator handle 700 extends axially outwardly of the first axial end 710 of the main body portion 702. The actuator portion 704 is an elongated rod. The actuator portion 704 may have gripping features located on an upper surface 724.

An actuator linkage 730 (FIG. 1) of the reduction device 512 has a generally rectangular shape that is defined between first and second axial ends 732 and 734, respectively. A first through-hole 736 extends laterally through the second axial end 734 of the actuator linkage 730. A second through-hole 738 extends laterally through the actuator linkage adjacent the first axial end 732.

A second actuation handle 740 includes a main body portion 742 and an axially extending actuator portion 744. The main body portion 742 of the actuator handle 740 includes a rounded lower surface 746, an upper surface 747, and planar first and second side surfaces 748. The main body portion 742 of the actuator handle 740 also includes first and second axial ends 750 and 752.

An axially extending channel 754 extends into the upper surface 747 of the actuator handle 740 to define first and second flanges 756 and 758. The first flange 756 extends between the first and second axial ends 750 and 752 of the main body portion 742 adjacent the first side surface. The second flange 758 extends between the first and second axial ends 750 and 752 of the main body portion 742 adjacent the second side surface 748. Coaxial through-holes 760 extend through the first and second flanges 756 and 758 adjacent the first axial end 750 of the main body portion 742. Coaxial through-holes 762 extend through the first and second flanges 756 and 758 adjacent the second axial end 752 of the main body portion 742.

The actuator portion 744 of the actuator handle 740 extends axially outwardly of the first axial end 750 of the main body portion 742. The actuator portion 744 is an elongated rod. The actuator portion may have gripping features located on a lower surface 764.

An actuator linkage 770 has a generally rectangular shape that is defined between first and second axial ends 772 and 774. A first through-hole 776 extends laterally through the first axial end 772. A second through-hole 778 extends laterally through tie actuator linkage adjacent the second axial end 774.

The reduction device 512 also includes a translating mechanism 780 (FIG. 11). The translating mechanism 780 includes a part or carriage 782. The part or carriage 782 extends axially between first and second axial ends 784 and 786. The carriage 782 is cylindrical. The carriage 782 is dimensioned to be received in the bore 684 of the fixed handle 650. The part or carriage 782 may have any desired shape.

An axially extending bore 794 extends through the part or carriage 784 between the first and second axial ends 784 and 786. A groove or slot 796 in the carriage 782 intersects the bore 794. The groove 796 extends radially though approximately 75% of the part or carriage 782. The part or carriage 782 includes an axially extending channel 797 which is open at the bottom. The channel 797 intersects the bore 794 and the groove 796. Fist and second through-holes 798 extend through the lower portion of the part or carriage 782 to connect to the channel 797. The first and second through-holes 798 are coaxial with one another.

To assemble the reduction device 512, the second linking element 638 of the actuator shaft 606 is inserted into the central channel 596 of the pivotal portion 584 of the pivotal jaw 580 and the through-hole 640 in the second linking element 638 is aligned with the through-holes 598 in the first and second members 592 and 594 of the pivotal portion 584 of the pivotal jaw 580. A pivot pin 800 (FIG. 26) is inserted through the aligned through-holes 598 and 640 and is secured to tie first and second members 592 and 594 of the pivotal portion 584 of the pivotal jaw 580. The pivot pin 800 enables the pivotal jaw 580 to pivot relative to the actuator shaft 606.

Next, each of the pivot elements 600 of the pivotal jaw 580 is inserted into the opening of a respective slot 554 and 556 that is open on the first axial end 522 of the fixed shaft 516. With the actuator shaft 606 angled upwardly away from the fixed shaft 516, as shown in FIG. 39, the pivotal jaw 580 is moved toward the second axial end 524 of the fixed shaft 516. The pivotal jaw 580 is moved into the position shown in FIG. 39 in which each of the pivot elements 600 is located adjacent the through-hole 550 and 552 of the slot 554 and 556, respectively, near the second axial end of 52, of the fixed shaft 516. The first axial end 522 of the fixed shaft 516 is then inserted into the bore 684 of the fixed handle 650 and the fixed shaft 516 is secured, for example by welding, to the fixed handle 650. After securing the fixed shaft 516 to the fixed handle 650, the actuator shaft 606 is moved downwardly from the position shown in FIG. 39 to the position shown in FIG. 40. During the downward movement of the actuator shaft 606, the pivotal jaw 580 is forced upwardly so that the pivot elements 600 of the pivotal jaw 580 become located in the through-holes 550 and 552. When located in the through-holes 550 and 552, the pivot elements 600 of the pivotal jaw 580 are prevented from moving axially relative to the fixed shaft 516. The pivotal jaw 580 and the fixed jaw 520, when connected together as shown in FIG. 40, collectively form a clamp 810.

The actuator shaft 606, when moved downwardly into the position shown in FIG. 40, is received within the channel 548 of the fixed shaft 516. When received in the channel 548 of the fixed shaft 516, the end surfaces 628 of the side walls 614 and 616 of the actuator shaft 606 rest on the first and second end surfaces 538 and 540 of the bottom wall 526 of the fixed shaft 516. Tie outer surfaces 626 of the side walls 614 and 616 of the actuator shaft 606 lie in the channel 548 of the fixed shaft 516 adjacent the inner surfaces 542 of the first and second side walls 528 and 530 of the fixed shaft 516. When the actuator shaft 606 is lying adjacent the fixed shaft 616 as shown in FIG. 40, the point 622 of the actuator shaft 606 and the point 536 of the fixed shaft 516 align on a central axis of a cylindrical passage 820 that is formed between the actuator shaft 606 and the fixed shaft 520.

When the actuator shaft 606 is moved downwardly into the channel 548 of the fixed shaft 516, the first linking element 630 of the actuator shaft 606 is received in the channel 664 of the fixed handle 650. The actuator shaft 606 is moved axially to align the through-hole 636 in the linking member 634 of the first linking element 630 With the through-holes 674 and 676 extending into the slots 670 and 672 in the fixed handle 650. The actuator handle 700 is then inserted into the channel 664 in the fixed handle 650 so that the linking member 34 of the first linking element 630 of the actuator shaft 606 is received in the channel 714 between the first and second flanges 716 and 718 of the actuator handle 700. The actuator handle 700 is moved to align the coaxial through-holes 722 adjacent the second axial end 712 of the actuator handle 700 with the through-hole 636 in of the actuator shaft 606 and the through-holes 674 and 676 of the fixed handle 650. A pivot pin 822 (FIG. 26) is then inserted through one of the through-holes 674 add 676 in the fixed handle 650 and into the through-holes 722 and 736 in the actuator handle 700 and the first linking element 730, respectively. When properly inserted, one end of the pivot pin 822 is located in the slot 670 of the side wall 660 of the fixed handle 650 and the other end of the pivot pin 822 is located in the slot 672 of the side wall 662 of the fixed handle 650. A center portion of the pivot pin 822 enables pivotal movement of the actuator handle 700 relative to the actuator shaft 606 about the pivot pin 822 while the ends of the pivot pin 822 are retained within the slots 670 and 672 of the fixed handle 650.

The second axial end 734 of the actuator linkage 730 is then inserted into the channel 714 of the actuator handle 700 and the through-hole 736 of the second axial end 734 of the actuator linkage 730 is aligned with the coaxial through-holes 720 adjacent the first axial end 710 of the actuator handle 700. A pivot pin 824 (FIG. 26) is inserted into the aligned through-holes 736 and 720 and is secured to the first and second flanges 716 and 718 of the actuator handle 700. The pivot pin 824 enables pivotal movement between the actuator linkage 730 and the actuator handle 700.

The through-hole 738 in the first axial end 732 of the actuator linkage 730 is then aligned with the through-holes 666 and 668 in the upper portions 660 and 662 of the fixed handle 650. A pivot pin 826 (FIG. 26) is inserted into the aligned through-holes 738, 666, and 668 and is secured to the upper portions 660 and 662 of the fixed handle 650. The pivot pin 826 enables pivotal movement of the actuator linkage 736 relative to the fixed handle 650 for opening and closing the clamp 810 of the reduction device 512.

The translating mechanism 780 is then assembled into the fixed handle 650. To assemble the translating mechanism 780 in the fixed handle 650, the part or carriage 782 is inserted into the cylindrical bore 684. The actuator handle 744 is then inserted into the channel 678 in the fixed handle 650 and is moved to align the coaxial through-holes 762 adjacent the second axial end 752 of the actuator handle 744 with the through-holes 680 and 682 of the fixed handle 650. A pivot pin 828 is then inserted through the through-holes 680 and 682 in the fixed handle 650 and the through-holes 762 in the actuator handle 740. A center portion of the pivot pin 828 enables pivotable movement of the actuator handle 744 relative to the fixed handle 650 about the pivot pin 828.

The second axial end 744 of the actuator linkage 770 is then inserted into the channel 678 in the fixed handle 650 and into the channel 797 in the carriage 782. The through-hole 778 of the second axial end 774 of the actuator linkage 770 is aligned with the coaxial through-holes 798 in the carriage 782. A pivot pin 830 is inserted into the aligned through-holes and is secured to the carriage 782. The pivot pin 830 enables pivotable movement between the actuator linkage 770 and the carriage 782.

The first axial end 772 of the actuator linkage 770 is then inserted into the channel 754 of the actuator handle 740 and the through-hole 774 of the second axial end 772 of the actuator linkage 770 is aligned with the coaxial through-holes 760 adjacent the first axial end 750 of the actuator handle 740. A pivot pin 832 is inserted into the aligned through-holes 776 and 760 and is secured to the first and second flanges 756 and 758 of the actuator handle 744. The pivot pin 832 enables pivotable movement between the actuator linkage 770 and the actuator handle 744.

Figure 41:
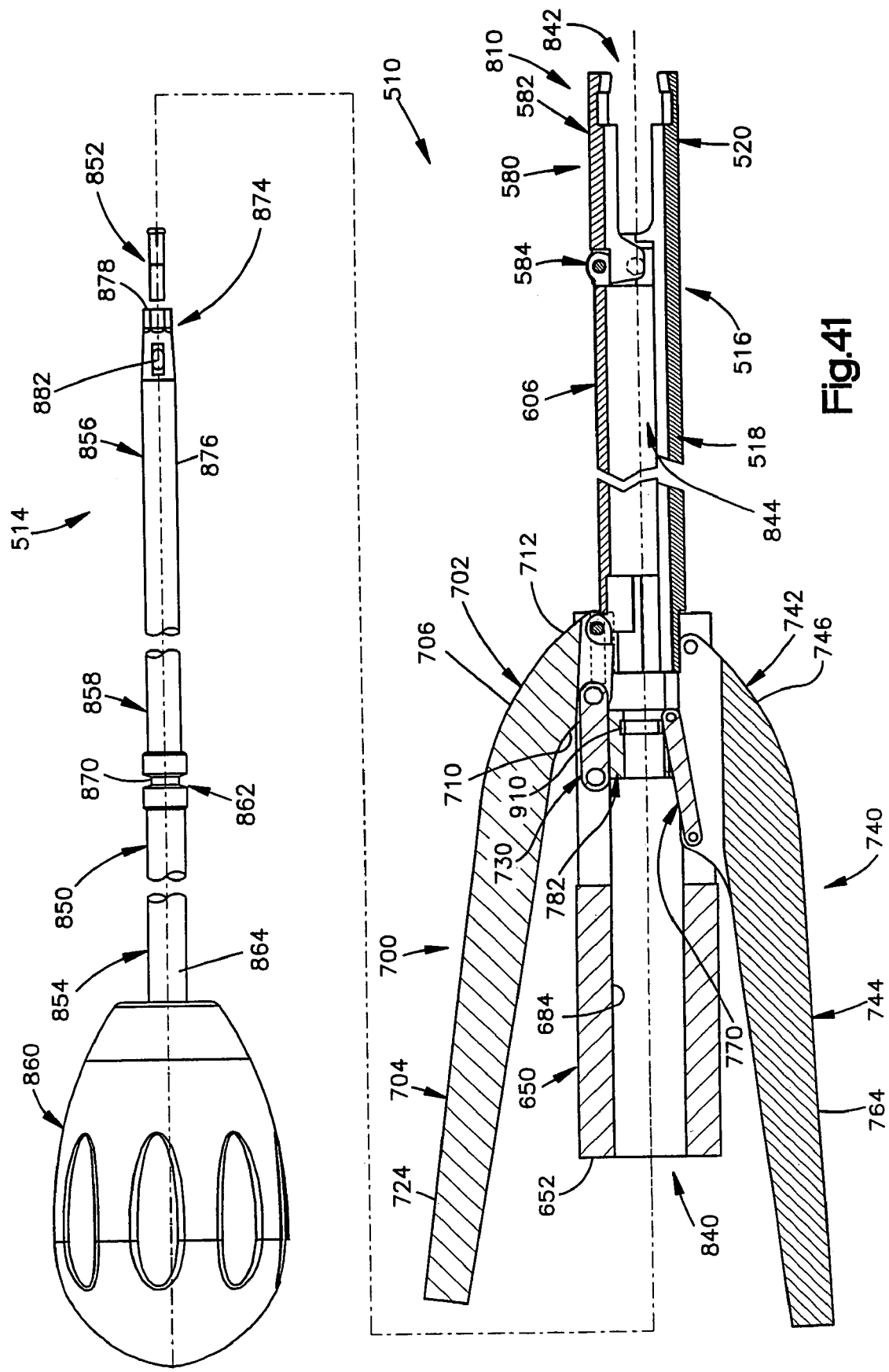
FIG. 41 is a side view, partially in section, of the surgical instrument of FIG. 26.
Figure 45:
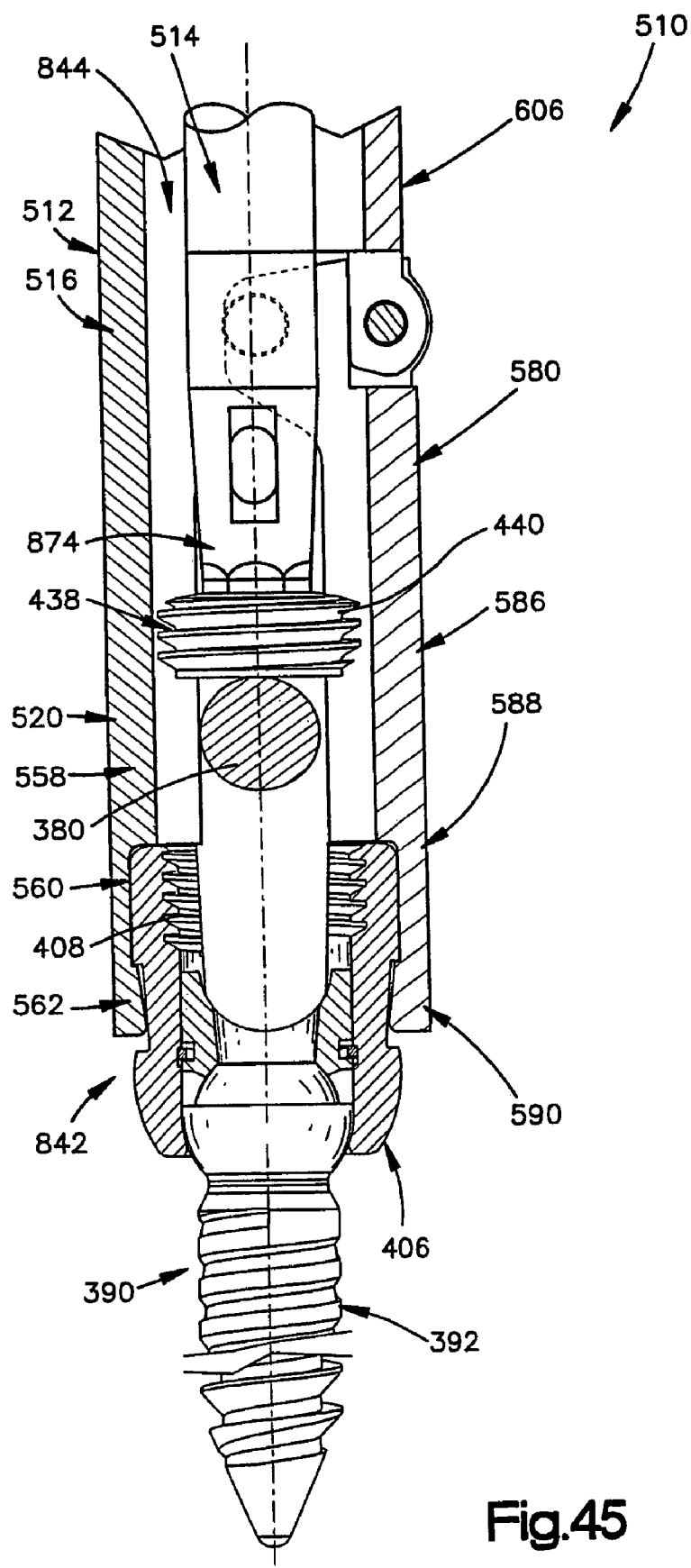
FIG. 45 illustrates a cross-sectional view of a portion of the surgical instrument of FIG. 26 being used in conjunction with a fastener.
Figure 46:
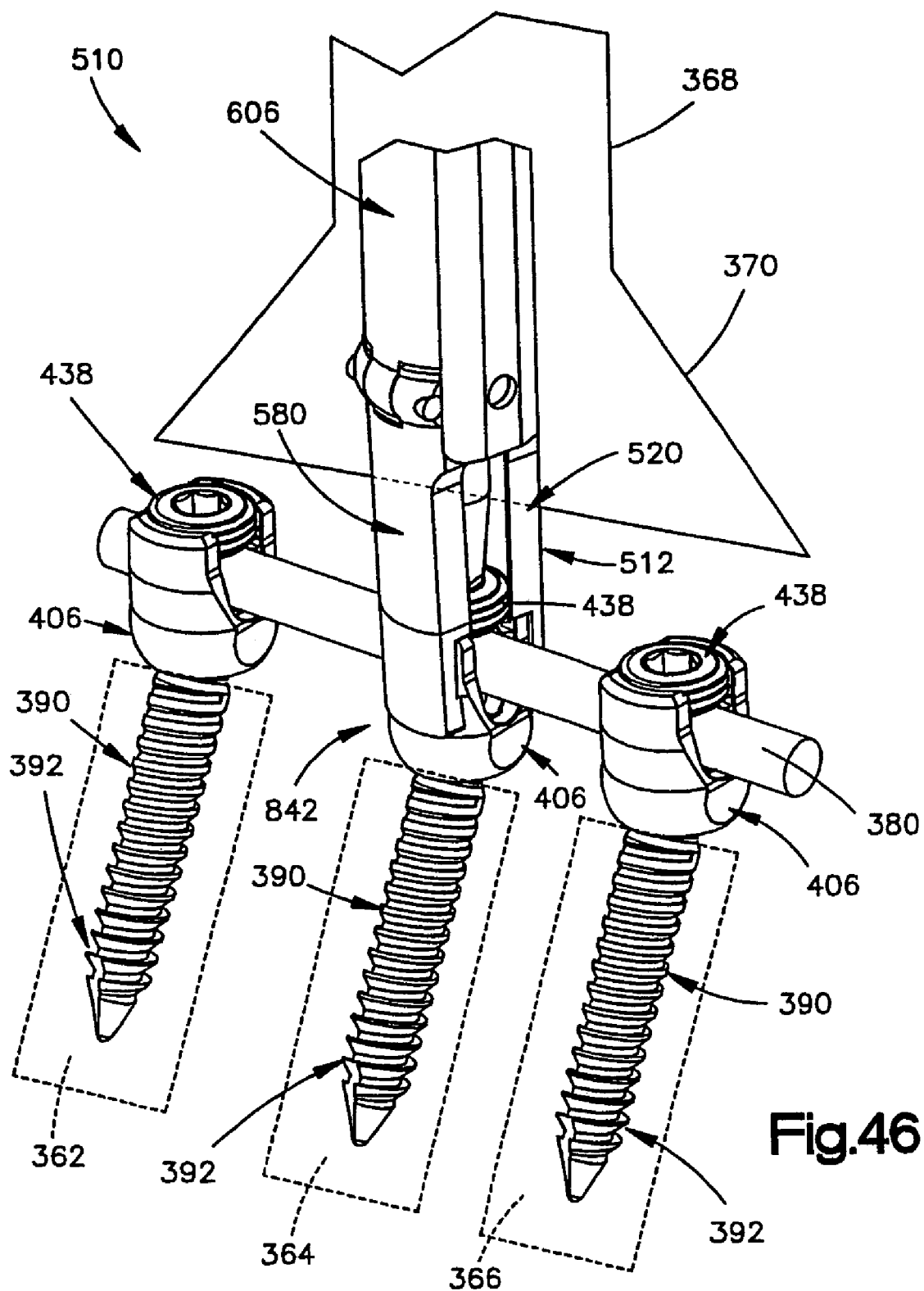
FIG. 46 illustrates the surgical instrument of FIG. 26 inserting a setscrew into the fastener to secure a vertebra to a rod.

The assembled reduction device 512 includes a proximal end 840 and a distal end 842. The proximal end 840 is located at the first axial end 652 of the fixed handle 650 and the distal end 842 is located at the clamp 810. A lumen 844 (FIG. 41) extends axially through the reduction device 512 from the proximal end 840 to the distal end 842. The bore 794 in the carriage 782 of the translating mechanism 780, the bore 684 in the fixed handle 650, and the passage 820 formed by the actuator shaft 606 and fixed shaft 516 define the lumen 844.

The drive device 514 (FIG. 26) includes a driver 850 and a driver spring 852. The driver 850 extends axially along axis A and includes first and second axial end portions 854 and 856, respectively, and an intermediate portion 858. The intermediate portion 858 of the driver 850 is a cylindrical shaft.

The first axial end portion 854 of the driver 850 includes a drive tool or ratcheting handle 860 and a drive portion 862. A cylindrical shaft 864 interconnects the drive tool 860 and the drive portion 862. The dive tool 860 is connected to the axial end portion 8 4 in any suitable manner. The drive portion 862 of the first axial end portion 854 of the driver 850 is cylindrical and has a larger diameter than the remainder of the driver 850. The drive portion 862 includes a radially inwardly extending annular groove 870.

The second axial end portion 856 of the driver 850 includes a drive portion 874. A cylindrical shaft 876 interconnects the drive portion 862 and the drive portion 874. The drive portion 874 of the second axial end portion 856 of the driver 850 is hexagonal. An end surface 878 (FIG. 37) of the drive portion 874 forms a second axial end of the driver 850.

As shown in FIG. 37, a cylindrical bore 880 extends into the end surface 878 at the second axial end of the driver 850. The bore 880 extends axially through the drive portion 874 and partially into the shaft 876 of the second axial end portion 856 of the driver 850. A window 882 extends radially through the shaft 876 of the second axial end portion 856 of the driver 850 and connects to the bore 880.

As shown in FIG. 37, the driver spring 852 includes a stepped shaft 890 and a head portion 892. The stepped shaft 890 includes first and second tubular portions 894 and 899. The first tubular portion 894 forms a first axial end of the driver spring 852 and connects to the second tubular portion 896. The second tubular portion 896 has an outer diameter that is slightly larger than an outer diameter of the first tubular portion 894 The inner diameters of the first and second tubular portions are the same and collectively form a passage 898 through the stepped shaft 890.

The head portion 892 of the driver spring 852 is connected to the second tubular portion 896 of the stepped shaft 890, opposite the first tubular portion 894. As shown in FIG. 38, the head portion 892 of the driver spring 852 is generally square and includes four side surfaces 900 and an end surface 902. Corners 904, connecting adjacent side surfaces 900, are rounded. The side surfaces 900 and the corners 904 taper radially inwardly toward the end surface 902. The taper of the corners 904 is greater than the taper of the side surfaces 900 so that the end surface 902 is generally circular.

An opening 906 extends through the center of the head portion 892 and connects to the passage 898 of the stepped shaft 890. The diameter of the opening 906 is the same as the inner diameters of the first and second tubular portions 894 and 896 of the stepped shaft 890.

Four grooves 918 extend axially through the head portion 892 and through a portion of the second tubular portion 896 of the driver spring 852. FIG. 37 shows one groove 908 extending axially through a portion of the second tubular portion 896 of the driver spring 852. In the head portion 892 of the driver spring 852, the four grooves 908 extend radially between the opening 906 and the side surfaces 900, as shown in FIG. 38. In the second tubular portion 896 of the driver spring 852, the four grooves 908 extend between the inner diameter and the outer diameter. Each side surface 910 of the head portion 892 has an associated groove 918. The associated groove 908 extends through the center of the side surface 900. The four grooves 908 enable the head portion 892 of the driver spring 852 to be compressed radially inwardly when subjected to a radially inwardly directed force. The head portion 892 resiliently returns to its original shape when the radially inwardly directed force is removed.

To assemble the drive device 514, the first tubular portion 894 of the driver spring 852 is inserted into the bore 880 on the second axial end of the driver 850. When the head portion 892 of the driver spring 852 is near the second axial end of the driver 850, the first tubular portion 894 of the driver spring 852 is fixed to the driver 850. Preferably, the first tubular portion 894 of the driver spring 852 is either soldered to or welded to the driver 850 with access to the first tubular portion 894 being provided through the window 882.

The drive device 514 is inserted into the lumen 844 in the reduction device 512. The driver device 514 is inserted into the reduction device 512 until the groove 870 is aligned with the groove 796 in the carriage 782. A retaining member or C-clip 910 is inserted through the groove 796 in the part or carriage 782 and into the groove 870 in the driver 850. The C-clip 910 extends radially from the groove 870 into the groove 796 to connect the drive device 514 to the reduction device 512. Accordingly, the drive device 514 and the carriage 782 move axially together relative to the fixed handle 650. The drive device 514 may also rotate relative to the carriage 782 and the reduction device 512.

The surgical instrument 510 of the present invention may be used for moving a vertebra relative to another vertebra, preferably along the sagittal plane of the body 360 during a surgical procedure. The surgical procedure may include open surgery. Preferably, the surgical procedure is performed through the structure or cannula 368.

FIG. 43 illustrates the three vertebrae 362, 364, and 366. Vertebra 364 is moved or slipped along the sagittal plane of the body 360 relative to vertebrae 362 and 366. FIG. 43 also illustrates the cannula 368 having the expandable distal end or skirt portion 370. The cannula 368 provides a passage into the body 360. The expanded skirt portion 370 of the cannula 360 defines an operative space that provides access to all three vertebrae 362, 364, and 366. An endoscope (not show) may be extended through the cannula 368 for providing vision within the operative space.

The surgical device 510 is used to move the vertebra 364 along the sagittal plane of the body 360 and connect the rod 380 to the fastener 390 secured to the vertebra 364 the rod 380 and fasteners 390 are identical to the rod and fasteners illustrated in FIGS. 17-25. Accordingly, the rod and fasteners will not be described in detail.

FIG. 42 shows a partial cross-section of the setscrew 438 of the fastener 390. A hexagonal bore 442 extends into an upper surface 444 of the setscrew 438. The hexagonal bore 442 is sized to receive the drive portion 874 of the second axial end portion 856 of the driver 850. A cylindrical bore 446, which is defined by cylindrical surface 448, extends into the setscrew 438 below the hexagonal bore 442. The cylindrical bore 446 and the hexagonal bore 442 are coaxial. A diameter of the cylindrical bore 446 is less than a width across the hexagonal bore 442 and is also less than the distance between rounded corners 904 of the head portion 892 of the driver spring 852.

The driver spring 852 holds the setscrew 438 on the drive device 514. The hexagonal drive portion 874 of the driver 850 is adapted to fit in the hexagonal bore 442 of the setscrew 438. When the drive portion 874 of the driver 850 is received in the hexagonal bore 852 of the setscrew 438, the driver spring 852 is received in the cylindrical bore 446 of the setscrew 438 for holding the setscrew on the drive device 514.

FIG. 42 illustrates the driver spring 852 holding the setscrew 438 on the drive device 514. When inserted into the cylindrical bore 446 of the setscrew 438, the side surfaces 900 of the driver spring 852 are forced together. The grooves 908 of the driver spring 852 enable the side surfaces 900 to move toward one another during axial movement of the driver spring 852 into the cylindrical bore 446. The four rounded corners 904 of the driver spring 852 press radially outwardly into contact with the cylindrical surface 448 defining the cylindrical bore 446 to hold the setscrew 438 on the drive device 514. To remove the setscrew 438 from the driver spring 852, the setscrew 438 is pulled axially off of the driver spring 852. The force of the driver spring 852 holding the setscrew 438 is sufficient to enable the setscrew 978 to be held vertically below the drive device 514.

As shown in FIG. 43, fasteners 390 are secured in each of the vertebrae 362, 364, and 366. The rod 380 extends between vertebrae 362 and 366 and is locked in place relative to vertebrae 362 and 366. As shown in FIG. 44, the housing 406 attached to the shank 392 of the fastener 390 secured in vertebra 364 is spaced, along the sagittal plane of the body 360, from the rod 380. The surgical instrument 510 of the present invention moves vertebra 364 along the sagittal plane of the body 360 and relative to vertebrae 362 and 366 so that the fastener 390 attached to vertebra 364 may be fastened to the rod 380.

To move vertebra 364 along the sagittal plane of the body 360, the distal end 842 of the reduction device 512 is inserted into the body 360 through the passage of the cannula 368. When the distal end 842 of the reduction device 512 is located in the operative space, the actuator handle 700 is pivoted away from the fixed handle 650 to move the actuator shaft 606 toward the proximal end 84 of the reduction device 512 and pivot the pivotal jaw 580 into an open position opening the clamp 810. The distal end 842 of the reduction device 512 is moved within the operative space to a position in which the rod 380 is located adjacent the inner surface 564 of the linking portion 558 of the fixed jaw 520 and the gripping portion 562 of the fixed jaw 520 is positioned in the circumferential groove 414 of the housing 406 attached to vertebra 364. When the gripping portion 562 of the fixed jaw 520 is positioned in the circumferential groove 414, the upper rim surface 420 of the housing 406 is received in the mouth portion 560 of the fixed jaw 520.

The actuator handle 700 is then pivoted toward the fixed handle 650 of the reduction device 512. As a result, the actuator shaft 606 is moved toward the distal end 842 of the reduction device 512 and the pivotal jaw 580 is closed or pivoted toward the fixed jaw 520 to close the clamp 810. During closure of the clamp 810, the distal end 842 of the reduction device 512 is manipulated so that the gripping portion 590 of the pivotal jaw 580 is positioned in the circumferential grove 414 of the housing 406 opposite the gripping portion 420 of the fixed jaw 406 and the upper rim surface 960 of the housing 946 is received in the mouth portion 588 of the pivotal jaw 580 opposite the mouth portion 560 of the fixed jaw 520. Thus, when the actuator handle 700 is pivoted toward the fixed handle 650, the housing 406 attached to vertebra 364 becomes locked in the clamp 810 formed between the fixed and pivotal jaws 520 and 580 of the reduction device 512 with the rod 380 located between the linking portions 558 and 586 of the fixed and pivotal jaws 520 and 580, respectively.

Figure 47:
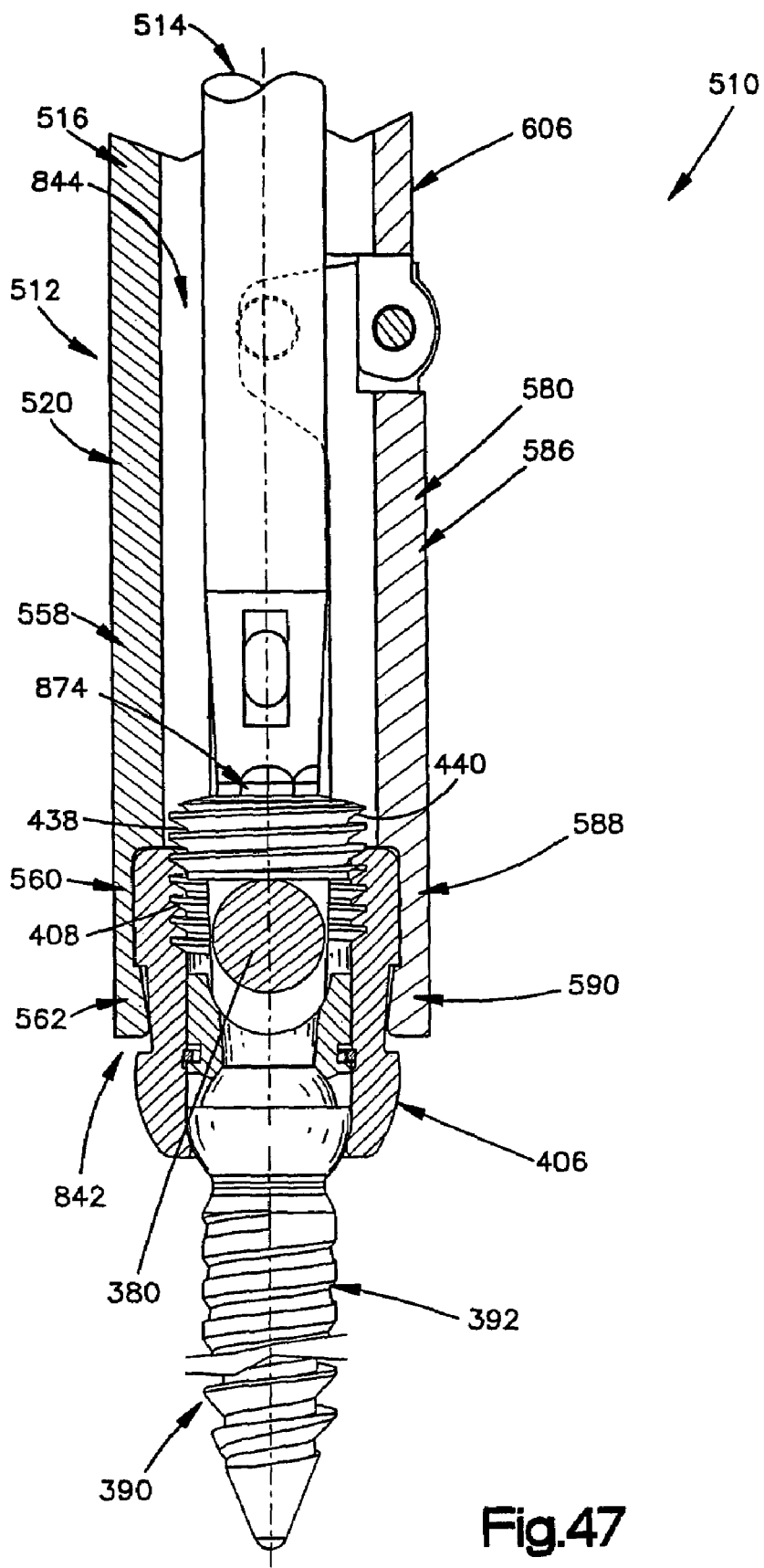
FIG. 47 is a cross-sectional view of a portion of the surgical instrument of FIG. 26 inserting a setscrew into the fastener to secure a vertebra to a rod.

The actuator handle 744 is pivoted toward the fixed handle 650. As a result, the drive device 514, with a setscrew 438 attached to the driver spring 852, is moved toward the distal end 842 of the reduction device. The drive device 514, which is holding on the setscrew 438, presses the setscrew 438 against the rod 380. The fastener 390 in vertebra 364 moves toward rod 380 and the vertebra 364 moves relative to vertebrae 362 and 366. Thus, the clamp 810 of the reduction device 512, which is clamped to the fastener 390 fixed to vertebra 364, is moved relative to the drive device 514 during movement of the drive device relative to the reduction device 512 so that the fastener 390 fixed to vertebra 364 is moved closer to the rod 380. Continued movement of the drive device 514 relative to the reduction device 512, moves vertebra 364 relative to vertebrae 362 and 366 and into a position in which the rod 380 is partially received in the housing 406 of the fastener 390 fixed to vertebra 364 and the threaded surface 408 of the housing 406 is brought into contact with the threaded outer surface 440 of the setscrew 438, as shown in FIG. 47.

When the threaded outer surface 440 of the setscrew 438 contacts the threaded inner surface 408 of the housing 406 of the fastener 390 fixed to vertebra 364, the drive device 514 is rotated relative to the reduction device 512. Relative rotation between the drive device 514 and the reduction device 512 results in rotation of the setscrew 438 relative to the housing 406 and moves the setscrew 438 axially into the housing 406 to lock vertebra 364 relative to the rod 380.

Misalignment of the threaded outer surface 440 of the setscrew 438 and the threaded inner surface 408 of the housing 406 may result. As a result, relative rotation between the drive device 514 and the reduction device 512 results in the setscrew 438 rotating relative to the housing 406 of the fastener 390 fixed to vertebra 364 but does not cause any translation or relative axial movement between the setscrew 438 and the housing 406. Rotation of the setscrew 438 without translation of the setscrew relative to the housing 406 enables proper alignment of the threaded surfaces 440 and 408 of the setscrew 438 and the housing 406 before the setscrew is screwed or threaded into the housing. As a result, cross-threading between the setscrew 438 and the housing 406 is prevented. When the threaded surfaces 440 and 408 of the setscrew 438 and the housing 406 are properly aligned, rotation of the drive device 514 screws or threads the setscrew 438 into the housing 406 to secure vertebra 364 to the rod 380.

Figure 48:
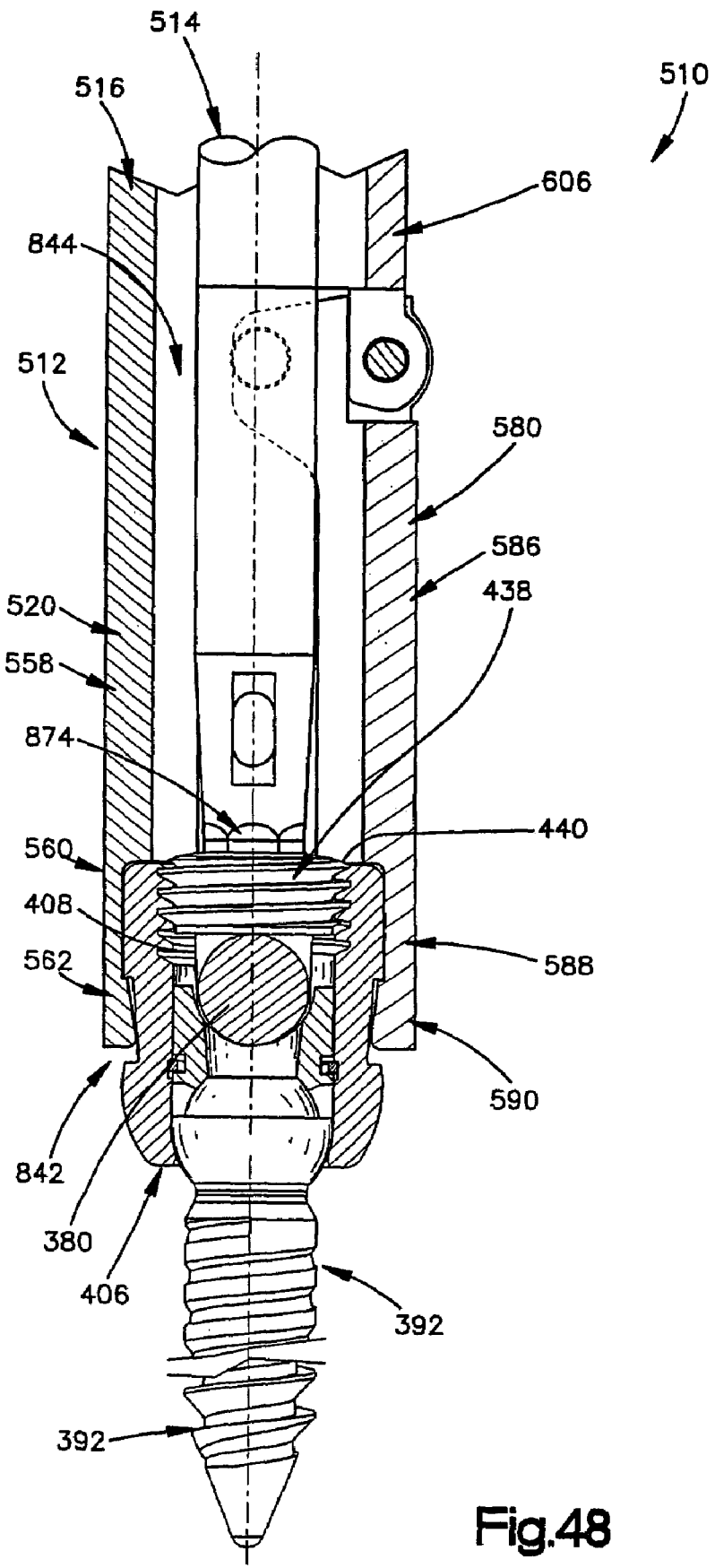
FIG. 48 is a cross-sectional view of a portion of the surgical instrument of FIG. 26 after complete insertion of the setscrew into the fastener to secure a vertebra to a rod.

When the setscrew 438 is secured in the housing 406 and vertebra 364 is secured to the rod 380, as is shown in FIG. 48, the actuator handle 740 is moved away from the fixed handle 650 to move the drive device 514 upwardly. The actuator handle 700 of the reduction device 512 is then moved away from the fixed handle 650 to pivot the pivotal jaw 580 and open the clamp 810. The reduction device 512 may then be removed from the housing 406 of the fastener 390, and removed from the cannula 368. Then, the cannula 368 may be removed from the body 360 and the body may be sutured in an appropriate manner.

The foregoing description sets forth various preferred embodiments and other exemplary but non-limiting embodiments of the inventions disclosed herein. The description gives some details regarding combinations and modes of the disclosed inventions. Other variations, combinations, modifications, modes, and/or applications of the disclosed features and aspects of the embodiments are also within the scope of this disclosure, including those that become apparent to those of skill in the art upon reading this specification. Thus, the scope of the inventions claimed herein should be determined only by a fair reading of the claims that follow.

What is claimed is:

1. A method of treating a spinal location of a patient, comprising:

providing an elongate body having a proximal end, a distal end, an outer surface and an inner surface, said elongate body defining a path extending therethrough;

inserting said distal end of said elongate body into the patient such that the distal end resides proximate the spinal location;

configuring said elongate body so that the cross-sectional area of said path at a first location is greater than the cross-sectional area of said path at a second location, wherein the first location is distal to the second location, wherein configuring said elongate body causes said outer surface to engage body tissue;

inserting a first screw into a first vertebra;

advancing through the path a device having a first portion including a clamp actuatable between open and closed positions, the clamp configured to engage the first screw coupled with the first vertebra and a second portion configured to manipulate a rod coupled to a second vertebra with a second screw, the first and second portions being aligned along a longitudinal axis of the device;

actuating the clamp to engage the first screw; and providing relative axial motion between the first and second portions of the device to move the first vertebra with respect to the second vertebra in a plane generally transverse to the spine of the patient while the cross-sectional area of the path at the first location remains greater than the cross-sectional area of the path at the second location.

2. The method of claim 1, wherein the elongate body is configured to provide access to at least three adjacent vertebrae of a patient.

3. The method of claim 1, further comprising extending an endoscope through the elongate body to provide vision within at least a portion of the path.

4. The method of claim 1, wherein the elongate body comprises an access device, the access device having an expandable distal end.

5. The method of claim 1, wherein the device is configured to limit the relative motion of the second portion along an axis generally transverse to the spine when a force applied by the device to the second portion exceeds a threshold level.

6. The method of claim 1, wherein providing relative motion between the first and second portion of the device comprises inserting the second portion within the first portion, and rotating the second portion relative to the first portion.

7. The method of claim 6, further comprising positioning a clamping member on a distal end of the second portion prior to inserting the second portion within the first portion.

8. The method of claim 1, wherein the clamp comprises a first jaw member and a second jaw member.

9. The method of claim 8, wherein at least one of the first jaw member and the second jaw member is pivotable relative to the other of the first and second jaw member to open and close the clamp.

10. A method for manipulating at least one of a first screw and a rod, comprising:

advancing an elongate body to a spinal location, the elongate body at least partially defining a path therethrough;

inserting the first screw into a first vertebra;

advancing through the path an instrument having a longitudinal axis and being configured to manipulate at least one of the first screw coupled with a first vertebra and the rod coupled to a second vertebra with a second screw, the instrument being configured to limit a force applied to the first screw or to the rod by the instrument along the longitudinal axis, the instrument including a clamp having first and second clamping portions, the first clamping portion being movable relative to the second clamping portion to actuate the clamp between open and closed positions;

moving the first clamping portion relative to the second clamping portion to engage the first screw; and moving the rod with respect to the first screw along the longitudinal axis to change the relative position of the first vertebra and the second vertebra in a plane generally transverse to the spine.

11. The method of claim 10, further comprising expanding a portion of the elongate body.

12. The method of claim 11, wherein expanding a portion of the elongate body comprises enlarging at least a distal portion of the elongate body such that an outer portion engages body tissue while the instrument moves the rod relative to the first screw.

13. A method for manipulating at least one of an anchoring member and an implant, comprising:

advancing an elongate body to a spinal location, the elongate body at least partially defining a path therethrough;

advancing through the path an instrument having a longitudinal axis and being configured to manipulate at least one of the anchoring member coupled with a first vertebra and the implant coupled with a second vertebra, the instrument being configured to limit a force applied to the anchoring member or to the implant by the instrument along the longitudinal axis the instrument including a spring configured to limit a force applied by the instrument along the axis; and moving the implant with respect to the anchoring member along the longitudinal axis to change the relative position of the first vertebra and the second vertebra in a plane generally transverse to the spine.

14. A method for manipulating at least one of an anchoring member and an implant, comprising:

advancing an elongate body through an incision to a spinal location to provide an access path to the spinal location through the incision, the elongate body having a distal end and a proximal end;

advancing along the access path an instrument having a longitudinal axis and being configured to apply an axial force not to exceed an upper threshotd along the axis, the instrument including a clamp having a first jaw member pivotable relative to a second jaw member, the clamp configured to engage the anchoring member when the first jaw member is pivoted towards the second jaw member;

engaging the anchoring member by pivoting the first jaw member towards the second jaw member; and applying an axial force with the instrument to move at least one of the anchoring member coupled with a first vertebra and the implant coupled with a second vertebra to change the relative position of the first vertebra and the second vertebra in a plane generally transverse to the spine.

15. The method of claim 14, wherein the elongate body defines a substantially enclosed path.

16. The method of claim 14, wherein the elongate body is expandable such that a transverse dimension at a first location is greater than a transverse dimension at a second location, wherein the first location is distal to the second location.

17. The method of claim 14, wherein the access path is sized such that more than one surgical instrument can be advanced simultaneously along the access path between the proximal end and the spinal location.

18. The method of claim 14, wherein the instrument comprises a spring, the spring being configured to be compressed when the axial force being applied by the instrument on at least one of the anchoring member and the implant reaches the threshold level.

19. A method of treating a spinal location of a patient, comprising:

providing an elongate body having a proximal end, a distal end, an outer surface and an inner surface, said elongate body defining a path extending therethrough;

inserting said distal end of said elongate body into the patient such that the distal end resides proximate the spinal location;

configuring said elongate body so that the cross-sectional area of said path at a first location is greater than the cross-sectional area of said path at a second location, wherein the first location is distal to the second location, wherein configuring said elongate body causes said outer surface to engage body tissue;

advancing through the path a device having a first portion configured to engage a first implant coupled with a first vertebra and a second portion configured to manipulate a second implant coupled with a second vertebra, the first portion including a first member moveable toward a second member to engage an implant;

engaging the first implant with the device by moving the first member toward the second member;

providing relative motion between the first and second portions of the device by inserting the second portion within the first portion and rotating the second portion relative to the first portion to move the first vertebra with respect to the second vertebra in a plane generally transverse to the spine of the patient while the cross-sectional area of the path at the first location remains greater than the cross-sectional area of the path at the second location; and positioning a clamping member on a distal end of the second portion prior to inserting the second portion within the first portion.

20. A method of treating a spinal location of a patient, comprising:

providing an elongate body having a proximal end, a distal end, an outer surface and an inner surface, said elongate body defining a path extending therethrough;

inserting said distal end of said elongate body into the patient such that the distal end resides proximate the spinal location;

configuring said elongate body so that the cross-sectional area of said path at a first location is greater than the cross-sectional area of said path at a second location, wherein the first location is distal to the second location, wherein configuring said elongate body causes said outer surface to engage body tissue;

advancing through the path a device having a first portion configured to engage a first implant coupled with a first vertebra and a second portion configured to manipulate a second implant coupled with a second vertebra, the first portion being a clamp, the clamp comprising a first jaw member pivotable relative to a second jaw member, the first and second portions being aligned along a longitudinal axis of the device;

engaging the first implant with the device by pivoting the first jaw member relative to the second jaw member; and providing relative axial motion between the first and second portions of the device to move the first vertebra with respect to the second vertebra in a plane generally transverse to the spine of the patient while the cross-sectional area of the path at the first location remains greater than the cross-sectional area of the path at the second location.

21. A method of treating a spinal location of a patient, comprising:

providing an elongate body having a proximal end, a distal end, an outer surface and an inner surface, said elongate body defining a path extending therethrough;

inserting said distal end of said elongate body into the patient such that the distal end resides proximate the spinal location;

configuring said elongate body so that the cross-sectional area of said path at a first location is greater than the cross-sectional area of said path at a second location, wherein the first location is distal to the second location, wherein configuring said elongate body causes said outer surface to engage body tissue;

advancing through the path a device having a first portion configured to engage a first implant coupled with a first vertebra and a second portion configured to manipulate a second implant coupled with a second vertebra, the first portion being a clamp, the clamp comprising a first jaw member and a second jaw member, wherein at least one of the first jaw member and the second jaw member is movable relative to the other of the first and second jaw member, the first and second portions being aligned along a longitudinal axis of the device;

engaging the first implant with the device by pivoting at least one of the first and second jaw members; and providing relative axial motion between the first and second portions of the device to move the first vertebra with respect to the second vertebra in a plane generally transverse to the spine of the patient while the cross-sectional area of the path at the first location remains greater than the cross-sectional area of the path at the second location.

* * * * *

UNITED STATES PATENT AND TRADEMARK OFFICE
CERTIFICATE OF CORRECTION

PATENT NO. : 7,618,444 B2 Page 1 of 1
APPLICATION NO. : 10/939935
DATED : November 17, 2009
INVENTOR(S) : Alan E. Shluzas It is certified that error appears in the above-identified patent and that said Letters Patent is hereby corrected as shown below:

Column 27
Line 48, delete "threshotd", and insert therefor -- threshold --.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,618,444 B2 Page 1 of 1
APPLICATION NO. : 10/939935
DATED : November 17, 2009
INVENTOR(S) : Alan E. Shluzas It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this

Twenty-sixth Day of October, 2010

David J. Kappos
*Director of the United States Patent and Trademark Office*